US009198961B2

(12) United States Patent
Bauer et al.

(10) Patent No.: US 9,198,961 B2
(45) Date of Patent: *Dec. 1, 2015

(54) BACTERIAL EXTRACT FOR DIGESTIVE OR URINARY TRACT DISORDERS AND PROCESS FOR ITS PREPARATION

(71) Applicant: OM PHARMA, Meyrin (CH)

(72) Inventors: Jacques Alain Bauer, Saint-Prex (CH); Marco Salvagni, Geneve (CH); Jean-Pierre Leon Vigroux, Bonneville (FR); Laetitia Chalvet, St. Genis Pouilly (FR); Carlo Chiavaroli, Thoiry (FR)

(73) Assignee: OM PHARMA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/597,254

(22) Filed: Jan. 15, 2015

(65) Prior Publication Data
US 2015/0174227 A1      Jun. 25, 2015

Related U.S. Application Data

(60) Continuation of application No. 13/528,520, filed on Jun. 20, 2012, now Pat. No. 9,017,743, which is a division of application No. 12/530,159, filed as application No. PCT/US2008/055902 on Mar. 5, 2008, now Pat. No. 8,236,522.

(60) Provisional application No. 60/904,787, filed on Mar. 5, 2007.

(51) Int. Cl.
*A61K 35/74*  (2015.01)
*A61K 39/00*  (2006.01)
*A61K 39/108* (2006.01)

(52) U.S. Cl.
CPC ............. *A61K 39/0258* (2013.01); *A61K 35/74* (2013.01); *A61K 2039/58* (2013.01); *Y10S 435/849* (2013.01)

(58) Field of Classification Search
None
See application file for complete search history.

(56) References Cited

U.S. PATENT DOCUMENTS

| | | | |
|---|---|---|---|
| 4,912,094 | A | 3/1990 | Myers et al. |
| 4,952,500 | A | 8/1990 | Finnerty et al. |
| 5,424,287 | A | 6/1995 | Bauer et al. |
| 6,346,252 | B1 | 2/2002 | Moigne |
| 2007/0026489 | A1 | 2/2007 | Leary et al. |
| 2007/0154492 | A1 | 7/2007 | Michon et al. |

FOREIGN PATENT DOCUMENTS

| | | |
|---|---|---|
| GB | 2054374 A | 2/1981 |
| JP | 03-039358 | 1/1993 |
| JP | 1993004929 | 1/1993 |
| JP | 1019940700540 | 12/1997 |
| WO | 89/07151 A1 | 8/1989 |
| WO | 93/16190 A1 | 8/1993 |

OTHER PUBLICATIONS

Chinese Office Action, Feb. 13, 2012, for Chinese Application No. 200880010610.2, filed Mar. 5, 2008.
European Office Action, Apr. 4, 2014, for OM PHARMA, European Application No. 08 731 429.0.
Supplemental European Search Report, Aug. 16, 2010, for European App'l No. 08731429.0, filed Mar. 5, 2008.
Israeli Office Action, Sep. 21, 2011, for Israeli App'l No. 200665, filed May 23, 2008.
Japanese Decision of Refusal, Mar. 19, 2013, Japanese Application No. 2009-552857 (English Translation).
Japanese Notice of Reasons for Refusal, Jan. 28, 2014, Japanese Application No. 2009-552857.
Japanese Decision of Refusal, Oct. 28, 2014, Japanese Application No. 2009-552857.
South Korea Notice of Submission of Opinion, Mar. 31, 2014, for OM PHARMA SA, South Korean Application No. 10-2009-7018711.
South Korea Notice of Submission of Opinion, Oct. 29, 2014, for OM PHARMA SA, South Korean Application No. 10-2009-7018711.
Russian Office Action, Aug. 12, 2011, for Russian App'l No. 2009136579, filed Oct. 2, 2009.
Taiwan Examination Report for OM PHARMA, Feb. 17, 2014, Taiwanese Application No. 097133418.
PCT Written Opinion of the International Searching Authority, Nov. 12, 2008, for Int'l App'l No. PCT/US2008/055902, filed Mar. 5, 2008.
PCT International Preliminary Report on Patentability, Sep. 8, 2009, for Int'l App'l No. PCT/US2008/055902, filed Mar. 5, 2008.
PCT International Search Report, Nov. 12, 2008, for Int'l App'l No. PCT/US2008/055902, filed Mar. 5, 2008.
Phil Smith, Converting today-Change of culture, Oct. 2005 (http://www.convertingtoday.co.uk./story.asp?storycode=35924) retrieved Apr. 27, 2011.
Introduction to Formulation of Protein Pharmaceuticals in Stability of Protein Pharmaceuticals, Part B: In Vivo Pathways of Degradation and Strategies for Protein Stabilization, 1992, edited by Tim J. Ahern and Mark C. Manning . . . Chapter 7, pp. 209-233.
"Miniprep. Plasmid purification", Apr. 9, 2006, http://homepage.ntu.edu.tw/~jmhu/hulab/protocols/Miniprep.pdf.
Quest International (www.sp2.uk.com Protein hydrolysates from non-animal sources for safer biotech medicines), Quest International, Nov. 2002.
Achor et al., 1981, "Effect of Treating Candida utilis with Acid or Alkali, to Remove Nucleic Acids, on the Quality of the Protein", J. Agric. Food Chem, 35:27-33.

(Continued)

*Primary Examiner* — Oluwatosin Ogunbiyi
(74) *Attorney, Agent, or Firm* — Law Offices of Albert Wai-Kit Chan, PLLC

(57) ABSTRACT

The present invention relates to an extract from bacterial strains useful as a treatment for disorders such as digestive or urinary tract disorders, compositions comprising the extract, and processes of making the extract from media that do not pose a risk of prion diseases.

13 Claims, 7 Drawing Sheets

(56) References Cited

OTHER PUBLICATIONS

Balen, A., 2002, Human Reproduction, 17: 1676-1680.

H.C. Birnboim and J. Doty, 1979, "A rapid alkaline extraction procedure for screening recombinant plasmid DNA", Nucleic Acids Research, 7(6):1513-1523.

Demain et al., 2005, "Effective Levels of Tetanus Toxin can be Made in a Production Medium Totally Lacking Both Animal (e.g. Brain Heart Infusion) and Dairy Proteins or Digests (e.g., Casein Hydrolysates)", Vaccine, vol. 23: 5420-5423.

Fang et al., 2009, "Production of Clostridium Difficile Toxin in a Medium Totally Free of Both Animal and Dairy Proteins or Digests", PNAS, vol. 106(32): 13225-13229.

Onier et al., 1993, "Involvement of T. Lymphocytes in Curative Effect of a New Immunomodulator OM 163 on Rat Colon Cancer Metastases", Eur. J. Cancer, vol. 29A (14): 2003-2009.

van Dijk et al., 1997, "Absorption, Kinetics, Antibody-bound and Free Serum Determination of a 14C-labeled *Escherichia coli* Extract After Single Oral Administration in Rats", Arzneim-Forsch, vol. 47(3): 329-334.

Wright et al., 2001, "Extraction of plasmid DNA using reactor scale alkaline lysis and selective precipitation for scalable transient transfection", Cytotechnology, 35: 165-173.

Canadian Office Action, Nov. 21, 2013, for OM PHARMA, Canadian Application No. 2,679,983.

U.S. Office Action, Sep. 2, 2010, for OM PHARMA, U.S. Appl. No. 12/530,159, filed Dec. 18, 2009.

U.S. Office Action, Dec. 7, 2010, for OM PHARMA, U.S. Appl. No. 12/530,159, filed Dec. 18, 2009.

U.S. Office Action, May 12, 2011, for OM PHARMA, U.S. Appl. No. 12/530,159, filed Dec. 18, 2009.

U.S. Office Action, Oct. 20, 2011, for OM PHARMA, U.S. Appl. No. 12/530,159, filed Dec. 18, 2009.

U.S. Office Action, Dec. 17, 2012, for OM PHARMA, U.S. Appl. No. 13/528,520, filed Jun. 20, 2012.

U.S. Office Action, Jun. 10, 2013, for OM PHARMA, U.S. Appl. No. 13/528,520, filed Jun. 20, 2012.

U.S. Office Action, Sep. 6, 2013, for OM PHARMA, U.S. Appl. No. 13/528,520, filed Jun. 20, 2012.

Japanese Pre-Appeal Examiner's Report dated Jul. 10, 2015, for Japanese Patent Application No. 2009-552857.

Bauer et al., 2005, "A long-term, multicenter, double-blind study of an *Escherichia coli* extract (OM-89) in female patients with recurrent urinary tract infections", Eur Urol., 47(4):542-8 (abstract only).

Huber et al., Mar. 27, 2000, "Immunostimulatory Activity of the Bacterial Extract (OM-89)", Eur J Med Res, 5:101-109.

BACTERIAL EXTRACT FOR DIGESTIVE OR URINARY TRACT DISORDERS AND PROCESS FOR ITS PREPARATION

DESCRIPTION OF THE INVENTION

This application is a Continuation application of U.S. Ser. No. 13/528,520, filed Jun. 20, 2012, now U.S. Pat. No. 9,017,743, issued Apr. 28, 2015, which is a Divisional application of U.S. Ser. No. 12/530,159, filed Dec. 18, 2009, now U.S. Pat. No. 8,236,522, issued Aug. 7, 2012, which is a National stage application of International Application No. PCT/US08/55902, filed Mar. 5, 2008, which claims the benefit of U.S. Ser. No. 60/904,787, filed Mar. 5, 2007. All of the preceding applications are incorporated herein by reference in their entireties into this application.

FIELD OF THE INVENTION

The present invention relates to extracts from bacterial strains useful as a treatment for indications such as digestive or urinary tract disorders, compositions comprising the extracts, and processes of making the extracts using media that do not pose a risk of prion diseases.

BACKGROUND AND SUMMARY OF THE INVENTION

The present invention relates to compositions comprising bacterial extracts useful for treating indications such as urinary tract or digestive disorders. The extracts may comprise bacterial lysates from cultures chosen from one or more species of *Escherichia coli*. In some embodiments, the extracts may comprise one or more species chosen from the following strains of *E. coli:* NCTC: 8603, 8621, 8622, 8623, 9026, 9111, 9119, 9707, and 9708 and I: 081, 082, 083, 084, 085, 086, 087, 088, and 089. Those strains are deposited under the Budapest Treaty. The strains indicated in the list with I-number were indexed by the Collection Nationale de Culture des Microorganismes at the Institut Pasteur, 25 rue du Dr. Roux, 75724 Paris, France. All of the other strains were indexed by the National Collection of Type Cultures in London.

In some embodiments, an extract is prepared from all of those strains. In other embodiments, only some of the strains are chosen. In some embodiments, for example, one or more strains is chosen from the "I" group and one or more strains is chosen from the "NCTC" group.

In some embodiments, one or more of the specific strains listed above may be omitted, or substituted with a different strain from *E. coli*, or from a different species of bacteria.

The extracts may be obtained by a process of alkaline lysis after cells are grown to a suitable optical density in a culture medium. In some embodiments, the bacteria are each grown on a medium that does not pose a risk of prion-related diseases or a risk of other diseases that may be transmitted through ingesting products obtained from animal-based media. For example, in some embodiments a vegetable-based medium is used to grow the cells, such as a soya-based medium. A synthetic medium may be used for cell growth in some embodiments, or a medium including biological extracts such as yeast extract and horse serum, which also do not pose such disease risks.

The lysates may also be filtered to remove nucleic acids and larger cellular debris. In consequence of the filtration, in some embodiments, the amount of nucleic acid present in the extracts is less than 100 μg/ml. In some embodiments, insolubilized compounds such as cell wall debris and insufficiently degraded lipopolysaccharide (LPS) are also removed by the filtration. Hence, in some embodiments, the resulting extract comprises soluble molecular components and does not contain significant amounts of insoluble or particulate material.

Saccharide components may be preserved in the extracts, including lipopolysaccharide (LPS) components. During the lysis process, saccharides may become chemically modified, for example, cleaved into smaller structures or substituted with other functional groups.

Racemization of amino acids during the lysis process also creates D-amino acids from the naturally occurring L-amino acids found in natural proteins. D-amino acids can be beneficial in increasing the time of effectiveness of the extracts, as they are not efficiently digested in the mammalian gut. Thus, antigenic molecules in the extracts that are chemically modified during lysis to contain D-amino acids remain in the patient's body for a longer time, allowing potentially for a stronger immunostimulating action.

While bacterial extracts have been used in the prior art to stimulate the immune system against digestive and urinary tract diseases, there has been a need to better standardize and control those extracts in order to make them safer, more effective, and longer lasting. For instance, it was previously thought that saccharide components, including potentially toxic lipopolysaccharide (LPS) components should be removed from bacterial extracts for safety reasons. (See, e.g., U.S. Pat. No. 5,424,287.) However, the instant invention provides a process that results in sufficient chemical modifications of LPS components that saccharides be safely retained. Retaining those components may improve efficacy as well by providing additional antigens.

For example, the inventors have discovered that monitoring the pH and the time of lysis allows for sufficient degradation of potentially allergenic or toxic cell wall components. Prior lysis conditions at lower pH's or shorter times, in contrast, produced extracts in which cell wall components and LPS were insufficiently chemically modified. (See, e.g., GB 2 054 374 A.) The resulting extracts were too allergenic to be safely administered to patients. In general, the inventors have discovered that products lysed at too low a pH and/or at too short a time had higher toxicity, lower protein extraction, and lower filterability.

In addition, the instant invention grows bacterial strains in culture media that do not pose disease risks, such as from prion diseases.

The filtration process can also influence the properties of the resulting extract in some cases, as the pore size of the filter, and sometimes, the chemical properties of the filter surface, alter the type of materials that are removed and retained. For example, the instant invention uses a filtration process that retains certain saccharides but removes other molecular components such as nucleic acids.

Thus, the instant invention provides parameters that standardize the bacterial extracts to help maintain consistent safety and efficacy.

DETAILED DESCRIPTION OF THE INVENTION

Definitions

Figure 1:
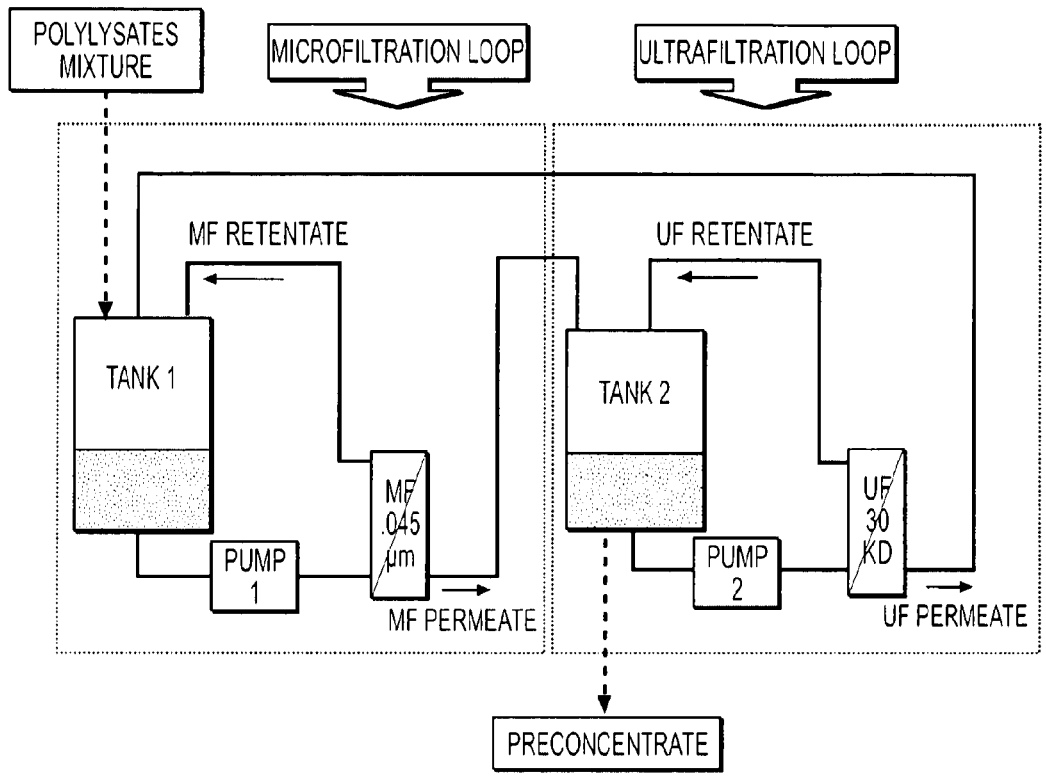
FIG. 1: A diagram of a tangential flow filtration (TFF) system for preparation of bacterial extracts following lysis of bacteria. The diagram shows two different configurations for filters: a parallel mode where all filters work simultaneously and a serpentine mode where filters are configured in a serial mode.
Figure 1:
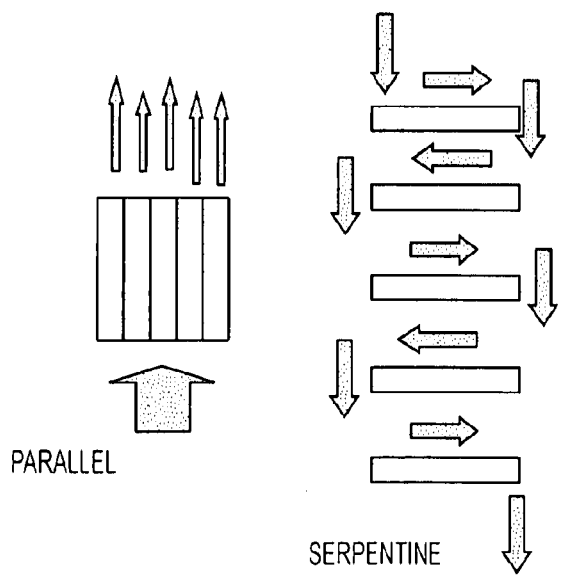

Extract: An extract, as defined herein, means material obtained following lysis of one or more bacterial strains. In some cases, the extract is obtained from only one strain while in others the extract is a mixture of extracts from several different strains.

Alkaline lysis: This is a method of lysing bacterial cells under basic conditions, such as using an organic or an inorganic base.

Lysate: An extract of bacteria obtained from a cell lysis procedure.

Filtration: A filtration process, as described herein, means a passage of an extract or a mixture of extracts, through one or more filters such as microfilters (i.e. microfiltration) or ultrafilters (i.e. ultrafiltration). Such filtration may not necessarily remove 100% of the components it is designed to remove. In some cases, filtration is repeated in several passes or cycles.

Initial pH: That term means the pH measured at the start of a procedure, such as bacterial lysis or filtration.

Saccharides: A saccharide, as defined herein, includes monosaccharides, disaccharides, as well as larger saccharides such as linear and branched polysaccharides. Saccharides also includes substituted or chemically modified saccharides, such as lipopolysaccharides (LPS) and their chemically modified variants.

D-amino acids: This term refers to amino acids that exist in dextra-rotatory isomeric forms, as opposed to biosynthetically produced L-amino acids, which exist in levo-rotatory isomeric forms.

Racemization: This term indicates at least partial chemical modification of L-amino acids to D-amino acids.

Medium that avoids the risk of prion-based diseases means a culture medium used at any stage of the preparation of the extracts that does not comprise materials such as serum or meat extracts taken from animals such as cows or sheep, or from any other animal that can transmit prion-based diseases. Examples of such media include vegetable-based or synthetic chemically defined media and also media using horse serum or media comprising materials taken from animals species that do not transmit prion diseases. Examples of prion-based diseases include, for example, mad cow disease, scrapie, and Creutzfeld-Jacob disease.

A non-animal medium is a medium that does not include components derived from animals. Examples include a vegetable-based (i.e. vegetal) medium, such as a soya medium, and a synthetic medium.

Treatment as used herein means both treatment of current infections and other conditions, for example, as well as prevention of or protection from the development of new infections, for example.

Subject, as used herein, means any animal subject, including mammalian subjects, such as humans and domestic mammals.

It is understood that the specific bacterial strains identified herein and used in the invention may include the strain obtained from the original deposit recited herein or a genetic clone thereof, including a strain that has been re-deposited at a later time with a different deposit code name, but which is considered to be genetically the same strain as the originally deposited version.

All numbers used herein are approximate, taking into account errors inherent in their measurement, rounding, and significant figures.

Preparation of Extracts

The bacterial extracts of the present invention may be prepared by fermentation followed by heat inactivation, concentration and harvest of biomass, alkaline lysis of single bacterial biomass or alkaline lysis of mixtures of bacterial biomass under defined conditions. The alkaline lysates under different conditions may be mixed prior to purification by filtration. The obtained filtrate may be further purified, such as to remove particulate matter, and may also be lyophilized and/or formulated.

For each strain, to obtain a sufficient amount of material, the fermentation cultures may be started from a working seed lot followed by inoculation into larger fermentation containers.

The media used may be the same for each species. However, supplementary growth factors may be introduced to enhance the growth of some species. In some embodiments, a medium that avoids the risk of prion-based diseases is used for growing at least some, or for all strains. Examples include non-animal media such as a vegetable-based medium and synthetic media. Other examples include a medium that includes horse serum or another animal extract, which is taken from a species of animal that does not pose a threat of prion diseases, in contrast to strains grown in the presence of bovine serum or meat extracts which can pose such risks.

In some embodiments, fermentation may start with a small culture such as 0.1 to 1.0 liter, incubated for about 3 to 6 hours at 30 to 40° C., such as 37° C., to obtain an optical density (OD) at 700 nm of 3.0 to 5.0. After a small-scale culture step, additional cultures in one or a series of larger fermenters may be performed at 30° C. to 40° C. for a duration of 3 hours to 20 hours, such as for 3-10 hours, or 8 hours.

After fermentation, the biomass from each strain or from a set of strains may be inactivated by a heat treatment, concentrated, and frozen. After thawing the frozen biomasses, the bacterial suspension may then be diluted and alkalinized to lyse the bacterial cells with a concentrated solution of hydroxide ions, such as from NaOH. In some embodiments, from about 10 to about 120 g/L of bacterial dry weight from one or a mix of strains is lysed, such as from about 15 to about 80 g/L, or from about 15 to about 35 g/L, such as 15, 20, 25, 30, or 35 g/L. In some embodiments, about 40 to about 80 g/L is lysed, such as 40, 50, 60, 70, or 80 g/L. (Bacterial dry weight concentration is defined by the amount of dry biomass per liter of lysis. The dry weight concentration is measured by drying 5 mL of material in a small porcelain dish at 105° C. until it reaches a constant mass and then recording the mass in grams per liter.) In some embodiments, a strong base concentration of 0.01 N to 1.2 N is used, such as, from 0.10 N to 1.1 N, or from 0.10 N to 0.65 N, or from 0.10 N to 0.4 N, or a range starting or ending from 0.1, 0.2, 0.3, or 0.4 N, or from 0.6 N to 1.1 N, or a range starting or ending from 0.6, 0.7, 0.8, 0.9, 1.0, or 1.1 N, or a base concentration is used so as to achieve an initial pH of 12 or higher, or a pH of greater than 12, a pH greater than 12 and less than 13.5, such as greater than 12.5, greater than 12.6, greater than 12.8, or from pH 12.6 to pH 13.4. The pH during the lysis may decrease upon the extraction of solubilized compounds. Thus, pH can be adjusted during the procedure. The lysis temperature may be from 30 to 60° C., such as from 35 to 40° C., such as 37° C. The time of lysis may vary from 20 hours to several days, such as 5, 6, 7, 8, 9, or 10 days, or from 30 to 120 hours, or from 30 to 50 hours, such as 30, 35, 40, 45, or 50 hours, or from 60 to 120 hours, such as 60, 72, 84, 96, 108, or 120 hours. The extracts may then be brought back to a lower pH, mixed together as desired, and filtered.

Following lysis, solubilized dry weight may be from 20 to 180 mg/mL. (The solubilized dry weight is determined by the same method as the bacterial dry weight described above and may alternatively be reported in mg/g units assuming that the density of the soluble lysate is 1g/mL.) The remaining protein concentration measured by the Lowry method, may be from 8 to 75 mg/mL, such as 10 to 70 mg/mL, 20 to 60 mg/mL, or a range starting or ending from 10, 15, 20, 25, 30, 35, 40, 45, 50, 55, 60, 65, or 70 mg/mL. The concentration of saccharides measured by the anthrone method for total reducing sugar, following lysis of a mixture of strains may be from 0.8 to 4 mg/mL, such as 1 to 3.5 mg/mL, 1.2 to 3 mg/mL, or a range starting or ending from 1, 1.5, 2, 2.5, 3, 3.5, or 4 mg/mL.

Lysis may be performed on only one strain at a time, or on a mix of all of the desired strains. For example, a mixed extract can be obtained by mixing, for instance, two or more bacterial lysates. Each such lysate might contain 10 g/L of biomass dry weight to 90 g/L, such as 15-85 g/L, or 20-80 g/L, or 25-75g/L, or 30-70 g/L, or 35-65 g/L or 40-60 g/L, or 15-35 g/L, or 40-80 g/L. Each such lysate may comprise, for example, from about 20% to 80% of the total extract by volume. The volume proportions of mixing the two lysates may be, for example, 25%-75%, or 75%-25%, 70%-30%, or 30%-70%, or 60%-40%, or 40%-60%, or 50-50%.

The lysates may then be purified by centrifugation and/or filtration. For example, lysates may be centrifuged at 9000× gravity, followed by one or more rounds of filtration on a 0.2 micron filter may be used to purify the extract. In some cases, successive rounds of filtration on larger pore filters followed by filtration on a 0.2 micron filter may be used. Ultrafiltration methods may also be employed in order to help extract soluble materials from the extract, for example, recirculating the ultrafiltration permeate for further microfiltration.

In some embodiments, a tangential flow filtration (TFF) method may be used to filter the extracts and to extract solubilized molecules from larger cellular debris. (See FIG. 1.) (See, e.g., Separations Technology, Pharmaceutical and Biotechnology Applications, Wayne P. Olson, Editor. Interpharm Press, Inc., Buffalo Grove, Ill., U.S.A., p. 126 to 135—ISBN: 0-935184-72-4.) At the beginning of such a TFF process, a diluted bacterial lysate may be stored in a first tank. A microfiltration (MF) loop is started, and the product is pumped and the resulting MF retentate is recycled, whereas the MF permeate is transferred to a second tank.

After reaching a suitable degree of concentration, an ultrafiltration (UF) loop is started. The UF permeate may be recirculated back to the first tank for continuous extraction of solubilized compounds from the lysate while the UF retentate may be stored in the second tank. During the continuous extraction, the volumes in tanks 1 and 2 may be adjusted by regulation of flow rates of the microfiltration and ultrafiltration permeates.

Several such extraction cycles may be performed, either with TFF or another filtration method. In embodiments that use TFF, at the end of the last cycle, the ultrafiltration loop may be shut down and the microfiltration loop may be run alone and the MF permeate transferred to tank 2.

The microfiltration loop may be fitted with filters of 1.2 microns to 0.1 microns, such as filters of 0.65 to 0.2 microns, or 0.45 microns. The cross-flow may be between 1000 Liters/hours $m^2$ (LHM) and 3000 LHM, such as between 1500 and 2500 LHM, or 2000 LHM with a trans-membrane pressure (TMP) of 0.6 to 2 bars, such as between 0.8 and 1.5 bars, or 1.0 bar. The ultrafiltration loop may be fitted with filters of from 10 KDa to 1000 KDa, such as from 10 KDa to 100 KDa, or from 10 KDa to 30 KDa, or from 30 KDa to 100 KDa. The cross-flow may be between 30 LHM and 1000 LHM, such as between 20 and 500 LHM with a TMP of 0.2 to 1.5 bars, such as between 0.4 and 1.2 bars, or 0.5 bar.

Between 5 and 20 diafiltration volumes may be used to extract solubilized compounds from bacterial cell walls. In some embodiments, between 8 and 15 volumes are used. Hence, for example, in some embodiments, between 5 and 15 cycles of filtration may be used, in some cases between 8 and 15 cycles, such as 8, 9. 10, 11, 12, 13, 14, or 15 cycles.

Following filtration, the extract may be further concentrated or centrifuged, if desired. For instance, a further microfiltration using a smaller pore filter may be performed, such as a 0.2 micron filter. After filtration, the yield of solubilized proteins measured by Lowry may be 50 to 90% or more than 60%. Following filtration, the extract may be lyophilized prior to formulating it for use.

In some embodiments of the invention, a selection of lysis conditions may be chosen so as to obtain a "strong" or "moderate" lysis. For instance, in some embodiments, a strong lysis may be achieved by lysing from about 15 to about 35 g/L bacterial dry weight, such as 15, 20, 25, 30, and 35 g/L or smaller ranges bounded by those concentrations (e.g. 15-20, 20-25, 20-30, etc.), with 0.6 to 1.1 N hydroxide ion, such as 0.6, 0.7, 0.8, 0.9, 1.0, or 1.1 N or smaller ranges bounded by those concentrations, for 60 to 120 hours, such as 60, 70, 80, 90, 100, 110, and 120 hours or smaller ranges bounded by those times, at 30-40° C., such as 35-40° C., 30-35° C., or 37° C. Thus, as used herein, a "strong" lysis involves the use of bacterial dry weight concentration, hydroxide ion concentration, time, and temperature falling within each of the broadest ranges above. In other embodiments, a moderate lysis may be achieved by lysing from about 40 to about 80 g/L bacterial dry weight (e.g. 40, 45, 50, 55, 60, 65, 70, 75, or 80) with 0.1 to 0.4 N hydroxide ion (i.e. 0.1, 0.2, 0.3, or 0.4) for 30 to 50 hours (e.g. 30, 35, 40, 45, or 50 hours) at 30-40° C., such as 35-40° C., 30-35° C., or 37° C. Hence, as used herein, a "moderate" lysis involves the use of bacterial dry weight concentration, hydroxide ion concentration, time, and temperature falling within each of the broadest ranges above. In some embodiments, a mixture of two bacterial lysates such as a strong and a moderate lysate as described above may be prepared, such as a 10% to 90% mixture, a 20/80, 25/75, 35/65, 50/50 mixture by volume. (See, for instance, examples 8 and 9 below.) In some embodiments, all of the strains to be used in the extract may be subjected to both a strong and a moderate lysis, followed by mixing the resulting lysates together. Or alternatively, some strains may be subjected to a strong lysis while others are subjected to a moderate lysis. Filtration of those lysates may occur before or after mixing, for example, by the TFF method through a MF loop with a 0.65 to 0.2 micron filter, such as a 0.6, 0.55, 0.5, 0.45, 0.4, 0.35, 0.3, or 0.25 micron filter and UF loop with a 10 or 30 KDa filter, for a total of 8 to 15 cycles, such as 8, 9, 10, 11, 12, 13, 14, or 15 cycles. Once prepared, extracts of the present invention may be purified to remove particulate matter.

Chemical Properties of Bacterial Extracts

Some embodiments according to the present invention may contain, for example, 5-75 mg/mL of proteins, or 10-65 mg/mL, or 20-45 mg/mL, or 5-40 mg/mL, or 5-20 mg/mL, of proteins or a range starting or ending from 5, 10, 15, 20, 25, 30, 35, 40, 45, 50, 55, 60, 65, 70 or 75 mg/mL; 1.5 to 2.5 mg/mL of free amino acids (A.A.), or 1.5 to 2 mg/mL, or 2 to 2.5 mg/mL of free A.A., or a range starting or ending from 1.5, 1.6, 1.7, 1.8, 1.9, 2.0, 2.1, 2.2, 2.3, 2.4, or 2.5 mg/mL of free A.A., calculated from glutamic acid (147.1 g/mol); and 0.3 to 4.5 mg/mL of polysaccharides and monosaccharides, or 0.3 to 4 mg/mL, or 0.4 to 4 mg/mL, or 0.5 to 3.5 mg/mL, or 0.6 to 3 mg/mL or 0.3 to 1 mg/mL or a range starting or ending from 0.3, 0.4, 0.5, 0.6, 0.7, 0.8, 0.9, 1.0, 1.5, 2.0, 2.5, 3.0, 3.5, 4.0, or 4.5 mg/mL of polysaccharides and monosaccharides. For example, some embodiments contain about 5 to 9 mg/mL of proteins, 2 mg/mL of free amino acids (A.A.), calculated from glutamic acid (147.1 g/mol) and/or about 0.3 to 0.6 mg/mL of polysaccharides and monosaccharides.

In some embodiments, the concentration of LPS equivalents based on a limulus amoebocyte lysate (LAL) chromogenic test is less than 5000 ng/mL, or less than 2000 ng/mL, or less than 1000 ng/mL, or less than 750 ng/mL, or less than 500 ng/mL, or less than 200 ng/mL, or less than 100 ng/mL.

Lysis of bacteria according to the present invention may result in partial hydrolysis of amphiphilic compounds such as lipopolysaccharides and lipopeptides. Lysis of bacteria according to the present invention may also result in partial hydrolysis of proteins as well as deamination, deamidation, and partial racemization of amino acids from L to D. In one analytical study of an extract according to the invention, after total HCl hydrolysis of the extract and derivatization of amino-acids, gas-chromatography peaks representing D-aspartic acid and D-asparagine, D-glutamic acid and D-glutamine, D-serine, D-methionine, D-histidine, D-alanine, D-arginine, D-phenylalanine, D-tyrosine, D-leucine, D-lysine, D-valine, D-threonine were each observed. The percentage of D-amino acids of those species in that study ranged from 3% to 80%. Hence, some embodiments of the invention allow for racemization of one or more of serine, methionine, aspartic acid and asparagine, threonine, histidine, alanine, arginine, tyrosine, phenylalanine, leucine, and lysine, such as all of the above amino acids, or any selection of more than one but less than all of the above amino acids, such as, for example, serine, asparatic acid, asparagine, alanine, phenylalanine, tyrosine, and lysine, or a selection of those amino acids. In some embodiments, at least 10% of one or more of the above amino acids may become racemized from L to D. In other embodiments, at least 30% of one or more of the above amino acids may become racemized.

Biological Activities of Bacterial Extracts

Extracts according to the invention may be effective to treat patients suffering from or at risk of developing urinary or digestive tract disorders such as digestive and urinary tract infections. Extracts according to the invention may be effective in preventing recurrent urinary tract infections. Examples of disorders that may be treated by extracts of the invention include *E. coli* and other bacterial infections, urethritis, tubulo-interstitial nephritis, obstructive pyelonephritis, urinary tract infections due to obstructive and reflux uropathy, cystitis including chronic cystitis, prostatitis including chronic prostatitis, prostatocystitis, female pelvic inflammatory diseases, Crohn's disease, and irritable bowel syndrome.

Biological activity of extracts may be determined by several assays. For example, a peripheral blood mononuclear cell (PBMC) assay tests the production of the cytokine IL-6 from PBMC's and can screen for the ability of an extract to stimulate the immune system. For example, in some embodiments, the in vitro IL-6 concentration measured in supernatants of PBMCs stimulated with the extracts of the invention ranged from 2000 pg/ml to 70,000 pg/ml, 2000 pg/ml to 50,000 pg/ml, 2000 pg/ml to 30,000 pg/ml, 2000 pg/ml to 20,000 pg/ml, 2000 pg/ml to 10,000 pg/ml, or 5000 pg/ml to 70,000 pg/ml, 5000 pg/ml to 50,000 pg/ml, 5000 pg/ml to 30,000 pg/ml, 5000 pg/ml to 25,000 pg/ml, or 5000 pg/ml to 10,000 pg/ml, or 15,000 pg/ml to 25,000 pg/ml. When LPS was used as an agonist control (at 0.01 µg/ml), the values obtained ranged, depending from the donors, from 5,000 pg/ml to 70,000 pg/ml.

A murine nitric oxide (NO) test measures production of NO by murine macrophages, which also indicates immune stimulation. For example, macrophages produce NO in order to kill invading bacteria. In some embodiments, in vitro nitrous oxide (NO) activity for embodiments of the present invention tested at concentrations ranging from 0.001 mg/ml to 10 mg/mi of soluble dry weight provided maximal responses ranging from 3 µM to 100 µµM nitric oxide, or 3 µM to 90 µM, 3µM to 80 µM, 3 µM to 70 µM, 3 µM to 60 µM, 3 µM to 50 µM, 3 µM to 40 µM, 3 µM to 30 µM, 3 µM to 20 µM, 3 µM to 10 µM, or 5 µM to 80 µM, 5 µM to 60 µM, 5 µM to 40 µM, 5 µM to 20 µM, or 10 µM to 80 µM, 10 µM to 70 µM, 10 µM to 50 µM, 10 to 30 µM, or 10 µM to 15 µM, or ranges beginning or ending from 3, 5, 10, 15, 20, 25, 30, 35, 40, 45, 50, 55, 60, 65, 70, 75, 80, 85, 90, 95, or 100 µM.

Activities observed on human peripheral blood mononuclear cells and murine macrophages in vitro may depend on variables such as the amount of bacterial dry weight to be lysed, i.e. the "starting material" for lysis, the duration of the alkaline lysis, and the initial percentage NaOH or initial pH used in the lysis.

Combination of in vitro activity tests such as PBMC and NO with determination of LPS concentration such as by LAL also may provide information concerning the balance of activity vs. toxicity risk for a given bacterial extract.

Activities observed in vivo on animals in infection models show that some embodiments of the present invention have a protective effect. See, for instance, example 9, showing repeated treatment of animals with exemplary extracts according to the invention. In an in vivo model of *E. coli* urinary tract infection (example 8), animals receiving preventively repeated oral administrations of exemplary extracts according to the invention display a lower amount of bacteria in the urinary tract (bladder and kidneys).

For example, the survival rate 13 days after challenge of at least 8 LPS-insensitive mice with uropathogenic *E. coli* strain 1677, is at least 60% when those mice are first treated for 10 days with effective amounts of some embodiments of the present invention. The dose of uropathogenic *E. coli* for the challenge may be chosen such that untreated mice or mice treated with a water or blank formulation control containing excipients but no extract have a survival rate of 60% or less, such as 50% or less. In some cases, the survival rate of mice treated with embodiments of the present invention in such a model is at least 70%, at least 80%, at least 80%, at least 90%, or at least 95%.

As another example, the survival rate 13 days after challenge of at least 8 mice having wild-type LPS sensitivity with *Salmonella thyphimurium*, is at least 60% when those mice are first treated for 10 days with effective amounts of some embodiments of the present invention. The dose of *Salmonella thyphimurium* for the challenge may be chosen such that untreated mice or mice treated with a water or blank formulation control containing excipients but no extract have a survival rate of 60% or less, such as 50% or less. In some cases, the survival rate for the extract-treated mice is at least 70%, at least 80%, at least 80%, at least 90%, or at least 95%.

Compositions Comprising the Bacterial Extracts

An extract according to the invention may be formulated in a number of different ways for eventual administration. For example, oral tablets, capsules, and pills may be prepared, as well as liquid formulations or aerosols. Formulations for infusion or injection may also be prepared.

Embodiments of this invention can be formulated, for example, as solid dosage forms or liquid dosage forms. Exemplary solid dosage forms may include, for example, a tablet, e.g. coated tablet, chewable tablet, effervescent tablet, sublingual tablet, granulates, powder, or a capsule) containing the extract, and optionally, one or more nutritional and/or dietary supplements. Solid dosage forms may also contain diluents, fillers, and/or other excipients. Other excipient components may be added such as preservatives, colorants, flavourings, and sweeteners. It is also possible to prepare powder or granulate formulations. Liquid dosage forms as solutions, syrups, suspensions, or drops can also be utilized for the oral route.

WORKING EXAMPLES

Example 1

Preparation of a Culture of *E. coli* Strains

The medium for *E. coli* I-081 (E81), *E. coli* I-082 (E82), *E. coli* I-083 (E83), *E. coli* I-084 (E84), *E. coli* I-085 (E85), *E. coli* I-086 (E86), *E. coli* I-087 (E87), *E. coli* I-088 (E88), *E. coli* I-089 (E89), *E. coli* NCTC 8603 (E8603), *E. coli* NCTC 8621 (E8621), *E. coli* NCTC 8622 (E8622), *E. coli* NCTC 8623 (E8623), *E. coli* NCTC 9026 (E9026), *E. coli* NCTC 9111 (E9111), *E. coli* NCTC 9119 (E9119), *E. coli* NCTC 9707 (E9707), and *E. coli* NCTC 9708 (E9708) was prepared by dissolving the following components in purified water: Sodium chloride 3.75 g/L; Sodium monohydrogenophosphate 2.5 g/L; Sodium acetate: 0.625 g/L; Vegetal peptone (Soya papaic digest) 50 g/L; Inosine 0.125 g/L; Calcium chloride 0.025 g/L; Potassium chloride 0.125 g/L; Sodium hydrogen carbonate 0.75 g/L; Arginine 1 g/L; Sodium pyruvate 0.35 g/L; Glucose 3 g/L; and a "solution of concentrated elements" 0.625 mL/L (which contains Copper sulfate 3 mg/l; Iron chloride 830 mg/l; Zinc sulfate 860 mg/l; and Sulfuric acid 1.1 mL/L.).

0.1 L of media was inoculated with 1.5 mL of frozen bacteria and incubated in a 300 mL Erlenmeyer flask at 37° C. for 4 hours with stirring. Then, 1.0 L of media in a 3000 mL Erlenmeyer was inoculated with 30 mL of the previous 300 mL culture and incubated again at 37° C. for 4 hours under stirring.

TABLE 1.1

OPTICAL DENSITY FOR SUCCESSIVE CULTURE STEPS

| | | OD ERLEN at 700 nm | | | |
|---|---|---|---|---|---|
| | Step | 100 mL 1 | 100 mL 2 | 1000 ml | 1000 ml |
| E8603 | Duration [hours] | 4 | 4 | 4 | 4 |
| | Culture 1 | 2.84 | 2.67 | 2.41 | 2.29 |
| E89 | Duration [hours] | 4 | 4 | 4 | 4 |
| | Culture 2 | 2.46 | 2.45 | 2.39 | 2.42 |
| E9111 | Duration [hours] | 5 | 5 | 4.25 | 4.25 |
| | Culture 3 | 3.13 | 2.92 | 2.45 | 2.50 |

The same media as above was prepared for prefermenters, but with the addition of 0.08 mL/L polypropylene glycol. One liter of the culture from the previous incubation step was transferred into the prefermenter. Incubation temperature was regulated at 30° C., and the prefermenter was stirred. pH was not regulated. Sterile air flow rate was adjusted to 3.3 L/min. After 6 hours, two prefermenters of 25 liters were transferred to a larger fermenter.

TABLE 1.2

OPTICAL DENSITY FOR PREFERMENTER CULTURES:

| Example number | Strain | Duration of culture [H] | OD at the end of culture Pref 1 [—] | OD at the end of culture Pref 2 [—] |
|---|---|---|---|---|
| Culture 1 | E8603 | 6 | 2.43 | 2.41 |
| Culture 2 | E89 | 6.75 | 1.95 | 2.05 |
| Culture 3 | E9111 | 12.25 | 2.00 | 2.45 |

The same media described above was prepared for the next incubation in larger-scale fermenters, but with addition of 0.05 mL/L polypropylene glycol and 6 g/L of glucose before sterilisation. Incubation temperature was regulated at 37° C., with stirring and aeration during the incubation. The pH was regulated at 6.8. Twelve Kg of glucose was added during the culture. After about 10.5 hours, the cultures were inactivated by heating to between 90 and 100° C. and transferred to a harvest tank. The biomass was then separated for the culture media and concentrated by centrifugation.

According to the described media and culture conditions, cultures were prepared, as shown in the tables and descriptions below.

TABLE 1.3

| Example Number | Strain | Duration of culture [h] | OD at end of growth at 700 nm | Total Volume [L] | Biomass Volume harvested [mL] | Volume of 1 aliquot [mL] | Biomass Dry weight [mg/mL] | Quantity of dry weight for 1 aliquot [g] |
|---|---|---|---|---|---|---|---|---|
| 1.2 | E81 | 5 | 18.72 | 498 | 61758 | 1196 | 168.4 | 201 |
| | | 5 | 17.84 | 498 | | | | |
| | | 5 | 18.28 | 497 | | | | |
| 1.3 | E82 | 8.5 | 23.52 | 491 | 69584 | 1062 | 176.6 | 188 |
| | | 8.00 | 22.52 | 491 | | | | |
| | | 7.75 | 17.08 | 489 | | | | |

TABLE 1.3-continued

| Example Number | Strain | Duration of culture [h] | Optic Density end of growth at 700 nm | Total Volume [L] | Biomasse Volume harvested [mL] | Volume of 1 aliquot [mL] | Dry weight [mg/mL] | quantity of dry weight for 1 aliquot [g] |
|---|---|---|---|---|---|---|---|---|
| 1.4 | E83 | 7 | 18.4 | 489 | 49275 | 1481 | 170.6 | 253 |
| | | 7 | 19.48 | 490 | | | | |
| | | 7 | 18.92 | 489 | | | | |
| 1.5 | E84 | 5.45 | 23.8 | 492 | 66647 | 928 | 182.9 | 170 |
| | | 5.45 | 21.08 | 466 | | | | |
| | | 5.45 | 23.2 | 492 | | | | |
| 1.6 | E85 | 7.5 | 21.28 | 493 | 73275 | 1262 | 183.4 | 224 |
| | | 7.5 | 20.4 | 494 | | | | |
| | | 8.5 | 20.52 | 494 | | | | |
| 1.7 | E86 | 4.75 | 19.960 | 491 | 66898 | 1116 | 168.9 | 188 |
| | | 4.75 | 20.840 | 491 | | | | |
| | | 4.75 | 19.200 | 491 | | | | |
| 1.8 | E87 | 5.25 | 21.24 | 490.5 | 73043 | 978 | 172.4 | 169 |
| | | 6.5 | 23.76 | 492.5 | | | | |
| | | 6.5 | 23.36 | 490.5 | | | | |
| 1.9 | E88 | 5.25 | 16.04 | 496 | 47478 | 906 | 151.6 | 137 |
| | | 5.25 | 15.2 | 494 | | | | |
| | | 5.25 | 15.4 | 492 | | | | |
| 1.10 | E89 | 5.5 | 12.00 | 489 | 46801 | 939 | 179.2 | 168 |
| | | 6.5 | 17.72 | 492 | | | | |
| | | 6.75 | 17.48 | 492 | | | | |
| 1.11 | E8621 | 5 | 23.3 | 493 | 64830 | 539 | 143.6 | 77.4 |
| | | 5 | 21 | 491.5 | | | | |
| | | 5 | 21.6 | 494 | | | | |
| 1.12 | E8622 | 4.75 | 19.36 | 492 | 67671 | 343 | 187 | 64 |
| | | 4.75 | 18.80 | 493 | | | | |
| | | 4.75 | 18.80 | 493 | | | | |
| 1.13 | E8623 | 4.75 | 24.36 | 498 | 75748 | 347 | 178 | 62 |
| | | 4.75 | 24.72 | 498 | | | | |
| | | 4.75 | 24.8 | 496 | | | | |
| 1.14 | E9026 | 4.75 | 28.32 | 492 | 63091 | 346 | 180.2 | 62 |
| | | 4.75 | 28.08 | 492 | | | | |
| | | 4.75 | 28.40 | 492 | | | | |
| 1.15 | E9111 | 4.75 | 14.36 | 489 | 41990 | 621 | 133.6 | 83 |
| | | 4.75 | 12.92 | 489 | | | | |
| | | 4.75 | 13.6 | 488 | | | | |
| 1.16 | E9119 | 4.5 | 28 | 493 | 58396 | 313 | 190.5 | 60 |
| | | 4.5 | 26.08 | 493 | | | | |
| | | 4.5 | 26.64 | 492 | | | | |
| 1.17 | E9707 | 4.5 | 20 | 492 | 83381 | 564 | 133.8 | 75 |
| | | 5.5 | 21.48 | 492.5 | | | | |
| | | 5.25 | 22.16 | 493 | | | | |
| 1.18 | E9708 | 4.75 | 20.24 | 492 | 71942 | 387 | 167.1 | 65 |
| | | 4.75 | 19.52 | 491.5 | | | | |
| | | 4.75 | 19.6 | 492 | | | | |
| 1.19 | E8603 | 5.75 | 23.2 | 491 | 76115 | 336 | 179.2 | 60 |
| | | 4.75 | 23.48 | 491 | | | | |
| | | 5 | 25.4 | 493 | | | | |

Example 1.20

NCTC9111 was cultivated with a synthetic medium in the same conditions as described in example 1.2. The medium was prepared by dissolving in 540 L of purified water: 0.2220 Kg of inosine, 0.3330 Kg of citric acid monohydrate, 1.4430 Kg of glutamic acid, 1.1655 Kg of ammonium chloride, 0.7825 Kg of magnesium sulfate.2 $H_2O$, 1.5096 Kg of potassium phosphate ($KH_2PO_4$), 0.3330 Kg of arginine, 0.1110 Kg of uracil, 0.0189 Kg of calcium chloride, 11.8200 Kg of sodium chloride, 0.5435 Kg of L-leucine, 0.5435 Kg of L-lysine HCL, 0.5435 Kg of L-serine, 0.5435 Kg of L-methionine, 0.5435 Kg of L-valine, 0.5435 Kg of L-alanine, 0.5435 Kg of L-asparagine, 14.0000 L ammonium hydroxide, 0.3420 L of potassium hydroxide, 40.5000 Kg of glucose, 4.1667 g of iron chloride, 4.1667 g of cobalt chloride, 4.1667 g of sodium molybdate, 4.1667 g of manganese sulfate, 4.1667 g of zinc sulfate, 4.1667 g of nickel sulfate, 0.0833 g of boric acid, 0.1667 g of copper sulfate, 1.8333 mL of sulfuric acid (95-97%).

Example 2

Alkaline Lysis of Cells

Example 2.1

One aliquot of each following strains E81, E82, E83, E084, E085, E086, E087, E088, E89, E9111, E 8603, E 8621, E 8622, E8623, E 026, E9119, E9707, and E9708 containing 1810 g of bacterial dry weight was thawed at room temperature, then diluted to with purified water to reach 26 g/L of bacterial biomass (dry weight). Alkalinization at 0.8 M sodium hydroxide was performed. pH was measured after 2 hours of lysis and was 13.1. Then the lysis was incubated for 120 hours at 35-40° C. under continuous stirring. After the incubation, the pH was adjusted to 11.3 with concentrated HCl. (Soluble Dry weight); SDW: 59.4 mg/mL; Prot: 17.4 mg/mL. The soluble dry weight was determined by obtaining 5 mL of the soluble fraction resulting from the lysis and drying it to a constant mass in a porcelain dish at 105° C.

Example 2.2

According to examples 1.1 to 1.19, 3 aliquots of E81, E82, E084, E086, E087, E89, 2 aliquots of E83 and E085, 4 aliquots of E088, 6 aliquots of E9111, 9 aliquots of E 8603, E9119, 7 aliquots of E8621, E9707 and 8 aliquots of E 8622, E8623, E9026, and E9708 containing a total of 9264 g of bacterial dry weight, were thawed at room temperature, then diluted with purified water, to reach 50.1 g/L of bacterial biomass concentration (dry weight). Alkalinization at 0.2 N hydroxide ion was 12.3. The lysis was incubated for 32 hours at 35-40° C. under continuous stirring. During the lysis, the pH was monitored so that it did not decrease more than 1.3 pH units. The pH was adjusted to 11.3 with adjunction of concentrated HCl. (Soluble Dry weight); SDW: 60.7 mg/mL; Prot: 32.0 mg/mL.

Example 2.3

According to Table 2, biomasses were diluted to 58 g/L of bacterial biomass concentration. Alkalinization at 0.4 M NaOH was performed. The lysis was incubated for 1 day at 35-40° C. under continuous stirring. (Soluble Dry weight); SDW: 96.8 mg/mL; Prot: 35.3 mg/mL.

Example 2.4

According to Table 2, biomasses were diluted to 92 g/L of bacterial biomass concentration. Alkalinization at 0.4 M was performed with NaOH at 10N. The lysis was incubated for 1 day at 35-40° C. under continuous stirring. SDW: 146.6 mg/mL; Prot: 62.9 mg/mL.

Example 2.5

According to Table 2, biomasses were diluted to 58 g/L of bacterial biomass concentration. Alkalinization at 0.4 M NaOH was performed. The lysis was incubated for 7 day at 35-40° C. under continuous stirring. SDW: 97.7mg/mL; Prot: 42.4 mg/mL.

Example 2.6

According to Table 2, biomasses were diluted to 92 g/L of bacterial biomass concentration. Alkalinization at 0.4 M NaOH was performed. The lysis was incubated for 7 day at 35-40° C. under continuous stirring. SDW: 153.0 mg/mL; Prot: 78.9 mg/mL.

Example 2.7

According to Table 2, biomasses were diluted to 58 g/L of bacterial biomass concentration. Alkalinization at 0.4 M NaOH was performed. The lysis was incubated for 3 day at 35-40° C. under continuous stirring. SDW: 98.6 mg/mL; Prot: 29.6 mg/mL.

Example 2.8

According to Table 2, biomasses were diluted to 92 g/L of bacterial biomass concentration. Alkalinization at 0.4 M NaOH was performed. The lysis was incubated for 3 day at 35-40° C. under continuous stirring. SDW: 127.4 mg/mL; Prot: 60 mg/mL.

Example 2.9

According to Table 2, biomasses were diluted to 43 g/L of bacterial biomass concentration. Alkalinization at 0.2 M NaOH was performed. The lysis was incubated for 168 hours at 35-40° C. under continuous stirring. SDW: 43.2 mg/mL; Prot: 8.2 mg/mL.

Example 2.10

According to Table 2, biomasses were diluted to 57 g/L of bacterial biomass concentration. Alkalinization at 0.4 M NaOH was performed. The lysis was incubated for 3 days at 35-40° C. under continuous stirring. SDW: 69.5 mg/mL; Prot: 20.2 mg/mL.

Example 2.11

According to Table 2, biomasses were diluted to 30 g/L of bacterial biomass concentration. Alkalinization at 1 M NaOH was performed. The lysis was incubated for 3 days at 35-40° C. under continuous stirring. SDW: 86.9 mg/mL; Prot: 13 mg/mL.

Example 2.12

According to Table 2, biomasses were diluted to 27 g/L of bacterial biomass concentration. Alkalinization at 1 M NaOH was performed. The lysis was incubated for 3 days at 35-40° C. under continuous stirring. SDW: 91.3 mg/mL; Prot: 11.8 mg/mL.

Example 2.13

According to Table 2, biomasses were diluted to 14 g/L of bacterial biomass concentration. Alkalinization at 0.1 M NaOH was performedr. The lysis was incubated for 1 day at 35-40° C. under continuous stirring. SDW: 25.2 mg/mL; Prot: 5.8 mg/mL.

Example 2.14

According to Table 2, biomasses were diluted to 14 g/L of bacterial biomass concentration. Alkalinization at 0.2 M NaOH was performed. The lysis was incubated for 3 days at 35-40° C. under continuous stirring. SDW: 26.6 mg/mL; Prot: 5.7 mg/mL.

Example 2.15

According to Table 2, biomasses were diluted to 14 g/L of bacterial biomass concentration. Alkalinization at 0.1 M NaOH was performed. The lysis was incubated for 10 days at 35-40° C. under continuous stirring. SDW: 20.0 mg/mL; Prot: 2.1 mg/mL.

Example 2.16

According to Table 2, biomasses were diluted to 114 g/L of bacterial biomass concentration. Alkalinization at 1 M NaOH was performed. The lysis was incubated for 1 day at 35-40° C. under continuous stirring. SDW: 163.3 mg/mL; Prot: 68.4 mg/mL.

Example 2.17

According to Table 2, biomasses were diluted to 114 g/L of bacterial biomass concentration. Alkalinization at 0.4 M NaOH was performed. The lysis was incubated for 3 days at 35-40° C. under continuous stirring. SDW: 163.0 mg/mL; Prot: 60.3 mg/mL.

Example 2.18

According to Table 2, biomasses were diluted to 114 g/L of bacterial biomass concentration. Alkalinization at 1 M NaOH was performed. The lysis was incubated for 10 days at 35-40° C. under continuous stirring. SDW: 171.2 mg/mL; Prot: 71.0 mg/mL.

Example 2.19

According to Table 2, biomasses were diluted to 25 g/L of bacterial biomass concentration. Alkalinization at 0.45 M NaOH was performed. The lysis was incubated for 4 days at 35-40° C. under continuous stirring. SDW: 48.5 mg/mL; Prot: 15.2 mg/mL; A.A: 4.0 mg/ml; Sugar: 0.86 mg/mL.

Example 2.20

According to Table 2, biomasses were diluted to 28 g/L of bacterial Biomass concentration. Alkalinization at 0.6 M NaOH was performed. The lysis was incubated for 4 days at 35-40° C. under continuous stirring. SDW: 59.4 mg/mL; Prot: 16.8 mg/mL; A.A: 5.4 mg/ml; Sugar: 1.22 mg/mL.

Example 2.21

According to Table 2, biomasses were diluted to 58 g/L of bacterial Biomass concentration. Alkalinization at 0.2 M NaOH was performed. The lysis was incubated for 4 days at 35-40° C. under continuous stirring. SDW: 64.4 mg/mL; Prot: 32.4 mg/mL; A.A: 5.6 mg/ml; Sugar: 1.84 mg/mL.

Example 2.22

According to Table 2, biomasses were diluted to 56 g/L of bacterial Biomass concentration. Alkalinization at 0.2 M NaOH was performed. The lysis was incubated for 3 days at 35-40° C. under continuous stirring. SDW: 61.0 mg/mL; Prot: 30.0 mg/mL; A.A: 5.6 mg/ml; Sugar: 1.88 mg/mL.

Example 2.23

According to Table 2, biomasses were diluted to 39 g/L of bacterial Biomass concentration. Alkalinization at 0.7 M NaOH was performed. The lysis was incubated for 4 days at 35-40° C. under continuous stirring. SDW: 78.32 mg/mL; Prot: 20.60 mg/mL; A.A: 7.8 mg/ml; Sugar: 1.54 mg/mL.

Example 2.24

One aliquot of each following strains E82, E83, E084, E086, E087, E088, E9111, E 8603, E 8621, E 8622, E8623, E 026, E9119, E9707, and E9708 containing 1810 g of bacterial dry weight was thawed at room temperature, then diluted with purified water to reach 25 g/L of bacterial biomass (dry weight). Alkalinization at 1.0 M sodium hydroxide was performed. pH was measured after 2 hours of lysis and was 13.5. Then the lysis was incubated for 72 hours at 35-40° C. under continuous stirring. After the incubation, the pH was adjusted to 11.4 with concentrated HCl. (Soluble Dry weight); SDW: 75.4 mg/mL; Prot: 14.8 mg/mL; A.A: 5.4 mg/ml; Sugar: 0.9 mg/mL.

TABLE 2

COMPOSITION OF *E. COLI* LYSES

| | E81 example 1.2 | E82 example 1.3 | E83 example 1.4 | E84 example 1.5 | E85 example 1.6 | E86 example 1.7 | E87 example 1.8 | E88 example 1.9 | E89 example 1.10 | E8603 example 1.11 |
|---|---|---|---|---|---|---|---|---|---|---|
| 2.3 | | | | | | | | | | |
| 2.4 | | | | | | | x | | | |
| 2.5 | | | | | | | | | | |
| 2.6 | | | | | | | x | | | |
| 2.7 | | | | | | | | | | x |
| 2.8 | x | x | x | x | x | x | x | x | x | |
| 2.9 | | | | | | | | | | |
| 2.10 | | | | | | | | | | |
| 2.11 | | | | | | | | | | x |
| 2.12 | x | x | x | x | x | x | x | x | x | |
| 2.13 | x | x | x | x | x | x | x | x | x | x |
| 2.14 | x | x | x | x | x | x | x | x | x | x |
| 2.15 | x | x | x | x | x | x | x | x | x | x |
| 2.16 | x | x | x | x | x | x | x | x | x | x |
| 2.17 | x | x | x | x | x | x | x | x | x | x |
| 2.18 | x | x | x | x | x | x | x | x | x | x |
| 2.19 | x | x | x | x | x | x | x | x | x | x |
| 2.20 | x | x | x | x | x | x | x | x | x | x |
| 2.21 | x | x | x | x | x | x | x | x | x | x |
| 2.22 | x | x | x | x | x | x | x | x | x | x |
| 2.23 | x | x | x | x | x | x | x | x | x | x |

| | E8621 example 1.12 | E8622 example 1.13 | 16E8623 example 1.14 | E9026 example 1.15 | E9111 example 1.16 | E9119 example 1.17 | E9707 example 1.18 | E9708 example 1.19 | E9111 example 1.20 |
|---|---|---|---|---|---|---|---|---|---|
| 2.3 | | | | | x | | | | |
| 2.4 | | | | | | | | | |
| 2.5 | | | | | x | | | | |
| 2.6 | | | | | | | | | |

TABLE 2-continued

COMPOSITION OF E. COLI LYSES

| | | | | | | | | |
|---|---|---|---|---|---|---|---|---|
| 2.7 | x | x | x | x | | x | x | x | |
| 2.8 | | | | | | | | | |
| 2.9 | | | | | | | | | x |
| 2.10 | | | | | | | | | x |
| 2.11 | x | x | x | x | | x | x | x | |
| 2.12 | | | | | | | | | |
| 2.13 | x | x | x | x | x | x | x | x | |
| 2.14 | x | x | x | x | x | x | x | x | |
| 2.15 | x | x | x | x | x | x | x | x | |
| 2.16 | x | x | x | x | x | x | x | x | |
| 2.17 | x | x | x | x | x | x | x | x | |
| 2.18 | x | x | x | x | x | x | x | x | |
| 2.19 | x | x | x | x | x | x | x | x | |
| 2.20 | x | x | x | x | x | x | x | x | |
| 2.21 | x | x | x | x | x | x | x | x | |
| 2.22 | x | x | x | x | x | x | x | x | |
| 2.23 | x | x | x | x | x | x | x | x | |

Example 3

Mixtures of Lysates

Several bacterial extracts were mixed and pH adjusted, with results below:

Example 3.1

0.845 Kg of E. coli Example 2.4 was mixed with 1.4 kg of E. coli Example 2.3. The mixture was diluted with purified water to 12 kg. The diluted bacterial lysate mixture was transferred to a microfiltration tank. The analytical results were Soluble Dry Weight (SDW): 29.7 mg/mL; Prot: 10.0 mg/mL.

Example 3.2

1.4 Kg of E. coli Example 2.7 was mixed with 0.85 kg of E. coli Example 2.8. The mixture was diluted with purified water to 12 kg. The diluted bacterial lysate mixture was transferred to a microfiltration tank. The analytical results were Soluble Dry Weight (SDW): 32.3 mg/mL; Prot: 10.3 mg/mL. SDW was measured as described in Example 2. Protein concentration was measured by a Lowry assay (see European Pharmacopoeia 2.5.33, under "total protein—method 2").

Example 3.3

1.4 Kg of E. coli Example 2.5 was mixed with 0.86 kg of E. coli Example 2.6. The mixture was diluted with purified water to 12 kg. The diluted bacterial lysate mixture was transferred to a microfiltration tank. The analytical results were SDW: 26.8 mg/mL; Prot: 9.6 mg/mL.

Example 3.4

2.4 Kg of E. coli Example 2.7 was mixed with 1.5 kg of E. coli Example 2.8. The mixture was diluted with purified water to 20 kg. The diluted bacterial lysate mixture was transferred to the microfiltration tank. The analytical results were SDW: 22.0 mg/mL; Prot: 9.5 mg/mL.

Example 3.5

9.0 Kg of E. coli Example 2.9 was diluted with purified water to 9.3 kg. The diluted bacterial lysate mixture was transferred to the microfiltration tank. The analytical results are SDW: 45.7 mg/mL; Prot: 20.6 mg/mL.

Example 3.6

8.1 Kg of E. coli Example 2.10 was diluted with purified water to 12 kg. The diluted bacterial lysate mixture was transferred to the microfiltration tank. The analytical results were SDW: 39.7 mg/mL; Prot: 17.3 mg/mL.

Example 3.7

3.2 Kg of E. coli Example 2.11 was mixed with 3.2 kg of E. coli Example 2.12. The mixture was diluted with purified water up to 12.8 kg. The diluted bacterial lysate mixture was transferred to the microfiltration tank. The analytical results were SDW: 39.9 mg/mL; Prot: 8.0 mg/mL.

Example 3.8

248 Kg of E. coli Example 2.19 was diluted with purified water to 400 kg. The diluted bacterial lysate mixture was transferred to the microfiltration tank. The analytical results are SDW: 31.6 mg/mL; Prot: 10.2 mg/mL; free amino acids (A.A.): 2.6 mg/mL; Sugar: 0.59 mg/mL. The sugar concentration was assayed after acid hydrolysis and derivatization according to D. Herbert et al., Meth. Microbiol. 5B: 266 et seq. (1971). The free amino acid concentration was measured by converting amino acids to isoindole derivatives and measuring absorbance at 340 nm, according to Roth M., Fluorescence reaction for amino acids, Anal. Chem., 43, 880-882, (1971). Results are expressed in equivalents of glutamic acid.

Example 3.9

248 Kg of E. coli Example 2.20 was diluted with purified water to 400 kg. The diluted bacterial lysate mixture was transferred to the microfiltration tank. The analytical results are SDW: 38.9 mg/mL; Prot: 10.8 mg/mL; A.A.: 3.6 mg/mL; Sugar: 0.74 mg/mL.

Example 3.10

247 Kg of E. coli Example 2.21 was diluted with purified water to 400 kg. The diluted bacterial lysate mixture was transferred to the microfiltration tank. The analytical results were SDW: 40.08 mg/mL; Prot: 20.0 mg/mL; A.A.: 3.6 mg/mL; Sugar: 1.17 mg/mL.

Example 3.11

247 Kg of E. coli Example 2.22 was diluted with purified water to 400 kg. The diluted bacterial lysate mixture was transferred to the microfiltration tank. The analytical results were SDW: 43.9 mg/mL; Prot: 19.1 mg/mL; amino acids (A.A.): 3.9 mg/mL; Sugars: 1.27 mg/mL.

Example 3.12

1.9 Kg of E. coli Example 2.21 was mixed with 6 kg of E. coli Example 2.23. The mixture was diluted with purified water to 12 kg. The diluted bacterial lysate mixture was transferred to the microfiltration tank. The analytical results were SDW: 45.4 mg/mL; Prot: 12.6 mg/mL; A.A.: 3.8 mg/mL; Sugar: 0.82 mg/mL.

Example 3.13

4 Kg of E. coli Example 2.21 was mixed with 4 kg of E. coli Example 2.23. The mixture was diluted with purified water to 12 kg. The diluted bacterial lysate mixture was transferred to the microfiltration tank. The analytical results were SDW: 47.0 mg/mL; Prot: 15.0 mg/mL; A.A.: 3.9 mg/mL; Sugar: 1.14 mg/mL.

Example 3.14

72.4 Kg of E. coli Example 2.1 was mixed with 185.2 kg of E. coli Example 2.2. The mixture was diluted with purified water to 400 kg. The diluted bacterial lysate mixture was transferred to the microfiltration tank. The analytical results were SDW: 40.8 mg/mL; Prot: 17.7 mg/mL; A.A.: 3.7 mg/mL; Sugar: 1.24 mg/mL.

Example 3.15

75.4 Kg of E. coli Example 2.24 was mixed with 185.2 kg of E. coli Example 2.2. The mixture was diluted with purified water to 400 kg. The diluted bacterial lysate mixture was transferred to the microfiltration tank. The analytical results were SDW: 43.6 mg/mL; Prot: 17.0 mg/mL; A.A.: 3.3 mg/mL; Sugar: 1.16 mg/mL.

Example 4

Purification of Lysates

Example 4.1

The bacterial lysate mixture of Example 3.1 was transferred into a microfiltration (MF) tank. The microfiltration (MF) unit used a 0.45 micron tangential flow filtration (TFF) filter (PALL Procette) in a serpentine mode or Schleicher & Schuell filter in parallel mode. (See FIG. 1 for an example diagram of a TFF set-up.) The cross flow, for serpentine mode was adjusted at 2000 L/h m² (LHM) and the Trans Membrane Pressure (TMP) at 1.3 bar. The permeate was transferred to an ultrafiltration (UF) tank.

Once the volume of the lysate in the microfiltration tank had reached one-half of the initial volume, the UF unit was started. The cross flow was adjusted to 1500 LHM and the TMP to 0.3 bar. The volumes of both the MF (Initial Volume of MF is called ViMF) and UF tanks were maintained at the same level. At each diafiltration volume (corresponding to ViMF), the protein extraction was followed by a measure of proteins by Bradford micro plaque assay. By this measurement, the number of extraction cycles was defined to extract all the solubilized compounds.

After 10 diafiltration volumes, the UF was stopped, and the bacterial lysate was concentrated in the MF tanks. The recovered volume was 9.55 kg. That product was then diluted to 7.0 mg/mL and then filtered through a 0.2 micron sterile filter. Soluble Dry Weight (SDW): 24.2 mg/mL; Prot: 6.4 mg/mL. A.A: 1.3 mg/mL, sugar: 0.5 mg/mL. D-amino acid percentage: 29% D-Ala, 4% D-Thr, 11% D-Leu, 45% D-Ser, 36% D-Asx, 29% D-Met, 26% D-Phe, 21% D-Glx, 25% D-Tyr, 9% D-Lys. NOx (macrophagic nitric oxide) production was measured after a 20,000-fold (C1), a 2000-fold (C2), and a 200-fold (C3) dilution with results as follows: C1: 6.3 µM, C2: 7.4 µM, and C3: 13.1 µM.

Several additional mixtures were filtered by Tangential Flow Filtration (TFF) as described below.

Example 4.2

The lysate of example 3.2 was transferred to an MF tank. The TFF installation was similar to example 4.1. The cross flow, for the serpentine mode was adjusted at 2500 LHM and the TMP at 1.30 bar. The UF was stopped after 10 diafiltration volumes and the permeate flow at the first cycle was 38.2 LHM. The dry weight extraction yield was 65%, protein extraction yield was 80% and the volume yield was 80%. The concentrate obtained comprised SDW: 26.1 mg/mL; Prot: 8.1 mg/mL; A.A.: 1.4 mg/mL; Sugar: 0.6 mg/mL; DNA: 4.8 µg/mL. D-amino acid percentage: 29% D-Ala, 4% D-Thr, 11% D-Leu, 45% D-Ser, 36% D-Asx, 29% D-Met, 26% D-Phe, 21% D-Glx, 25% D-Tyr, 9% D-Lys. NOx production after 20,000-fold (C1), 2000-fold (C2), and 200-fold (C3) dilution: C1: 5.5 µM, C2: 7.5 µM, C3: 5.5 µM.

Example 4.3

The lysate of example 3.3 was transferred to an MF tank. The TFF installation was similar to example 4.1. The cross flow, for the serpentine mode was adjusted at 2450 (L/h m²) LHM and the (Trans Membrane Pressure) TMP at 1.3 bar. The UF was stopped after 10 diafiltration volumes and the permeate flow at the first cycle was 26.2 L/h.m². The dry weight extraction yield was 65%, protein extraction yield was 75% and the volume yield was 88%. The concentrate obtained comprised SDW: 24.5 mg/mL; Prot: 7.0 mg/mL; A.A.: 2.1 mg/mL; Sugar: 0.5 mg/mL; DNA: 8.2 µg/mL. D-amino acid percentage: 45% D-Ala, 11% D-Leu, 48% D-Ser, 44% D-Asx, 41% D-Met, 26% D-Phe, 25% D-Glx, 38% D-Tyr, 27% D-Lys. NOx production after 20,000-fold (C1), 2000-fold (C2), and 200-fold (C3) dilution: C1: 5.1 µM, C2: 6.8 µM, C3: 13.7 µM.

Example 4.4

The lysate of example 3.4 was transferred to an MF tank. The TFF installation was similar to example 4.1. The cross flow, for the serpentine mode was adjusted at 2000 (L/h m²) LHM and the Trans Membrane Pressure) TMP at 1.8 bar. The UF was stopped after 10 diafiltration volumes and the permeate flow at the first cycle was 22.5 L/h.m². The dry weight extraction yield was 67%, protein extraction yield was 84% and the volume yield was 92%. The concentrate obtained comprised SDW: 21.5 mg/mL; Prot: 6.1 mg/mL; A.A.: 1.5 mg/mL; Sugar: 0.3 mg/mL; DNA: 5.6 µg/mL. D-amino acid percentage: 44% D-Ala, 15% D-Thr, 12% D-Leu, 48% D-Ser, 40% D-Asx, 40% D-Met, 30% D-Phe, 26% D-Glx, 31% D-Tyr, 18% D-Lys.

Example 4.5

The lysate of example 3.5 was transferred to an MF tank. The TFF installation was similar to example 4.1. The cross flow, for the serpentine mode was adjusted at 2000 (L/h m$^2$) LHM and the Trans Membrane Pressure) TMP at 1.3 bar. The UF was stopped after 10 diafiltration volumes and the permeate flow at the first cycle was 27.7 L/h.m$^2$. The dry weight extraction yield was 72%, protein extraction yield was 69% and the volume yield was 86%. The concentrate obtained comprised SDW: 36.9 mg/mL; Prot: 16.9 mg/mL; A.A.: 2.8 mg/mL; Sugar: 0.815 mg/mL; DNA: 46.7 µg/mL. D-amino acid percentage: 27% D-Ala, 16% D-Thr, 11% D-Leu, 48% D-Ser, 40% D-Asx, 39% D-Met, 36% D-Phe, 32% D-Glx, 31% D-Tyr. NOx production after 20,000-fold (C1), 2000-fold (C2), and 200-fold (C3) dilution: C1: 6.2 µM, C2: 10.9 µM, C3: 18.3 µM.

Example 4.6

The lysate of example 3.6 was transferred to an MF tank. The TFF installation was similar to example 4.1. The cross flow, for the serpentine mode was adjusted at 2000 (L/h m$^2$) LHM and the (Trans Membrane Pressure) TMP at 1.3 bar. The UF was stopped after 10 diafiltration volumes and the permeate flow at the first cycle was 15.7 L/h.m$^2$. The dry weight extraction yield was 53%, protein extraction yield was 51% and the volume yield was 81%. The concentrate obtained comprised SDW: 30.1 mg/mL; Prot: 12.7 mg/mL; A.A.: 2.6 mg/mL; Sugar: 0.364 mg/mL. D-amino acid percentage: 40% D-Ala, 16% D-Thr, 12% D-Leu, 49% D-Ser, 43% D-Asx, 44% D-Met, 40% D-Phe, 38% D-Glx, 36% D-Tyr, 24% D-Lys. NOx production after 20,000-fold (C1), 2000-fold (C2), and 200-fold (C3) dilution: C1: 5.8 µM, C2: 7.1 µM, C3: 15.1 µM.

Example 4.7

The lysate of example 3.7 was transferred to an MF tank. The TFF installation was similar to example 4.1. The cross flow, for the serpentine mode was adjusted at 2000 (L/h m$^2$) LHM and the (Trans Membrane Pressure) TMP at 1.35 bar. The UF was stopped after 10 diafiltration volumes and the permeate flow at the first cycle was 30.0 L/h.m$^2$. The dry weight extraction yield was 82%, protein extraction yield was 83% and the volume yield was 92%. The concentrate obtained comprised SDW: 38.2 mg/mL; Prot: 5.4 mg/mL. NOx production after 20,000-fold (C1), 2000-fold (C2), and 200-fold (C3) dilution: C1: 0.4 µM, C2: 2.1 µM, C3: 16.3 µM.

Example 4.8

500 ml of the lysate of example 2.13 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 45%. The concentrate obtained comprised SDW: 25.21 mg/mL; Prot: 5.85 mg/mL; DNA: 7.5 µg/mL. D-amino acid percentage: 24% D-Ala, 16% D-Thr, 9% D-Leu, 43% D-Ser, 20% D-Asx, 16% D-Met, 10% D-Phe, 8% D-Glx, 7% D-Tyr.

Example 4.9

500 ml of the lysate of example 2.14 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 53%. The concentrate obtained comprised SDW: 26.62 mg/mL; Prot: 5.75 mg/mL; DNA: 6.5 µg/mL. D-amino acid percentage: 35% D-Ala, 22% D-Thr, 10% D-Leu, 45% D-Ser, 35% D-Asx, 35% D-Met, 31% D-Phe, 24% D-Glx, 22% D-Tyr, 12% D-Lys. PBMC at 1 mg of active dry weight/mL: IL-6: 9232 µg/mL.

Example 4.10

500 ml of the lysate of example 2.15 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 53%. The concentrate obtained comprised SDW: 20 mg/mL; Prot: 2.13 mg/mL; DNA: 3.5 µg/mL. D-amino acid percentage: 35% D-Ala, 4% D-Thr, 11% D-Leu, 46% D-Ser, 34% D-Asx, 32% D-Met, 24% D-Phe, 24% D-Glx, 15% D-Tyr. NOx production in mg of active dry weight/mL: 0.01 mg/mL (C1), 0.1 mg/mL (C2), and 1.0 mg/mL (C3); C1: 3.6 µM, C2: 4.4 µM, C3: 7.9 µM.

Example 4.11

500 ml of the lysate of example 2.16 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 33%. The concentrate obtained comprised SDW: 163.33 mg/mL; Prot: 68.42 mg/mL; DNA: 14.1 µg/mL. D-amino acid percentage: 38% D-Thr, 1% D-Leu, 49% D-Ser, 43% D-Asx, 64% D-Met, 30% D-Phe, 31% D-Glx, 4% D-Tyr.

Example 4.12

500 ml of the lysate of example 2.17 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 17%. The concentrate obtained comprised SDW: 162.78 mg/mL; Prot: 60.26 mg/mL; DNA: 14.8 µg/mL. D-amino acid percentage: 10% D-Leu, 40% D-Ser, 34% D-Asx, 62% D-Met, 27% D-Phe, 23% D-Glx, 5% D-Tyr.

Example 4.13

500 ml of the lysate of example 2.18 was centrifuged for 30 minutes at 9000 g. Then supernatant was filtered through successive filters with porosities of 0.8 µm, 0.45 µm and 0.2 µm. pH was adjusted to 10.5 with HCl. The volume yield was 13%. The concentrate obtained comprised SDW: 171.16 mg/mL; Prot: 71.02 mg/mL; DNA: 16.9 µg/mL.

Example 4.14

The lysate of example 3.8 was transferred to an MF tank. The TFF installation was similar to example 4.1. The cross flow, for the serpentine mode, was adjusted at 2300 (L/h m$^2$) LHM and the Trans Membrane Pressure) TMP at 1.5 bar. The UF was stopped after 11 diafiltration volumes and the permeate flow at the first cycle was 32.5 L/h.m$^2$. The dry weight extraction yield was 86%, protein extraction yield was 87% and the volume yield was 90%. The concentrate obtained comprised SDW: 26.6 mg/mL; Prot: 8.1 mg/mL; .A.A.: 2.3 mg/mL; Sugar: 0.42 mg/mL; DNA: 68.5 µg/mL. PBMC at 1 mg of active dry weight/mL: IL-6: 29898 µg/mL, IL-10: 446 µg/ml, TNF-α: 3429 µg/mL. NOx production in mg of active dry weight/mL: 0.02 mg/mL (C1), 0.2 mg/mL (C2), and 2.0 mg/mL (C3); C1: 2.3 µM, C2: 16.6 µM, C3: 4.0 µM.

Example 4.15

The lysate of example 3.9 was transferred to an MF tank. The TFF installation was similar to example 4.1. The cross flow, for the serpentine mode was adjusted at 2375 (L/h m²) LHM and the Trans Membrane Pressure) TMP at 1.3 bar. The UF was stopped after 10 diafiltration volumes and the permeate flow at the first cycle was 32.5 L/h.m². The dry weight extraction yield was 83%, protein extraction yield was 79% and the volume yield was 92%. The concentrate obtained comprised SDW: 24.9 mg/mL; Prot: 7.2 mg/mL; .A.A.: 2.3 mg/mL; Sugar: 0.49 mg/mL. PBMC at 1 mg of active dry weight/mL: IL-6: 23709 µg/mL, IL-10: 385 µg/ml, TNF-α: 2917 µg/mL. NOx production in mg of active dry weight/mL: 0.02 mg/mL (C1), 0.2 mg/mL (C2), and 2.0 mg/mL (C3); C1: 1.1 µM, C2: 13.8 µM, C3: 4.2 µM.

Example 4.16

The lysate of example 3.10 was transferred to an MF tank. The TFF installation was similar to example 4.1. The cross flow, for the serpentine mode was adjusted at 2500 (L/h m²) LHM and the Trans Membrane Pressure) TMP at 1.0 bar. The UF was stopped after 10 diafiltration volumes and the permeate flow at the first cycle was 15.0 L/h.m². The dry weight extraction yield was 58%, protein extraction yield was 59% and the volume yield was 79%. The concentrate obtained comprised SDW: 22.0 mg/mL; Prot: 8.1 mg/mL; .A.A.: 1.6 mg/mL; Sugar: 0.46 mg/mL; DNA: 23.9 µg/mL. PBMC at 1 mg of active dry weight/mL: IL-6: 21458 µg/mL, IL-10: 281 pg/ml, TNF-α: 123 µg/mL. NOx production in mg of active dry weight/mL: 0.02 mg/mL (C1), 0.2 mg/mL (C2), and 2.0 mg/mL (C3); C1: 14.6 µM C2: 23.8 µM, C3: 16.9 µM. D-amino acid percentage: 27% D-Ala, 22% D-Thr, 11% D-Leu, 44% D-Ser, 27% D-Asx, 26% D-Met, 22% D-Phe, 16% D-Glx, 15% D-Tyr, 8% D-Lys.

Example 4.17

The lysate of example 3.11 was transferred to an MF tank. The TFF installation was similar to example 4.1. The cross flow, for the serpentine mode was adjusted at 2500 (L/h m²) LHM and the Trans Membrane Pressure) TMP at 1.0 bar. The UF was stopped after 10 diafiltration volumes and the permeate flow at the first cycle was 17.5 L/h.m². The dry weight extraction yield was 69%, protein extraction yield was 69% and the volume yield was 78%. The concentrate obtained comprised SDW: 22.2 mg/mL; Prot: 8.3 mg/mL; .A.A.: 1.8 mg/mL; Sugar: 0.5 mg/mL; DNA: 33.3 µg/mL. PBMC at 1 mg of active dry weight/mL: IL-6: 19304 µg/mL, IL-10: 343 µg/ml, TNF-α: 220 µg/mL. NOx production in mg of active dry weight/mL: 0.02 mg/mL (C1, 0.2 mg/mL (C2) and 2.0 mg/mL (C3); C1: 14.4 µM C2: 20.5 µM C3: 18.9 µM. D-amino acid percentage: 30% D-Ala, 18% D-Thr, 10% D-Leu, 44% D-Ser, 29% D-Asx, 28% D-Met, 23% D-Phe, 18% D-Glx, 18% D-Tyr, 11% D-Lys.

Seventy liters of the liquid form were neutralized with 196 mL of HCl 25% and then mixed with 10.44 kg of mannitol. Then the mixture was lyophilized. During the lyophilization cycle the product was frozen at −50° C. then warmed to −25° C. Pressure in the freeze-dryer was maintained between 0.2 and 0.5 mbar and controlled by means of filtered air injections. Then, in the secondary desiccation, the product was warmed up to its final lyophilization temperature (+30° C.) while keeping a vacuum level below 0.2 mbar. When the lyophilization cycle was complete, normal pressure was re-established in the freeze dryer with filtered air. The lyophilizate was sifted through a fitted vibrating sieve. 11.95 kg of lyophilizate were recovered.

Example 4.18

500 ml of the lysate of example 3.13 was centrifuged for 30 minutes at 9000 g. Then supernatant was filtered through successive filters with porosities of 0.8 µm, 0.45 µm and 0.2 µm. pH was adjusted to 10.5 with HCl. The concentrate obtained comprised SDW: 42.8 mg/mL; Prot: 12.5 mg/mL; A.A.: 3.5 mg/mL; Sugar: 1.13 mg/mL; DNA: 14.1 µg/mL. NOx production after 20,000-fold (C1), 2000-fold (C2), and 200-fold (C3) dilution: C1: 0.4 µM C2: 5.7 µM C3: 25.1 µM. PBMC for diluted volume mL of concentrate: Dilution 100: IL-6: 2101 pg/mL. D-amino acid percentage: 25% D-Ala, 12% D-Thr, 10% D-Leu, 45% D-Ser, 35% D-Asx, 35% D-Met, 29% D-Phe, 26% D-Glx.

Example 4.19

500 ml of the lysate of example 3.12 was centrifuged for 30 minutes at 9000 g. Then supernatant was filtered through successive filters with porosities of 0.8 µm, 0.45 µm and 0.2 µm. pH was adjusted to 10.5 with HCL. The concentrate obtained comprised SDW: 38 mg/mL; Prot: 9.7 mg/mL; A.A.: 3.1 mg/mL; Sugar: 0.82 mg/mL; DNA: 80.1 µg/mL. NOx production after 20,000-fold (C1), 2000-fold (C2), and 200-fold (C3) dilution: C1: 0.3 µM, C2: 2.6 µM, C3: 19.2 µM. PBMC for diluted volume mL of concentrate: Dilution 100: IL-6: 2802 pg/mL. D-amino acid percentage: 35% D-Ala, 25% D-Thr, 10% D-Leu, 46% D-Ser, 40% D-Asx, 38% D-Met, 34% D-Phe, 32% D-Glx, 32% D-Tyr, 24% D-Lys.

Example 4.20

The lysate of example 3.14 was transferred to an MF tank. The TFF installation was similar to example 4.1. The cross flow, for the serpentine mode, was adjusted at 2500 (L/h m²) LHM and the Trans Membrane Pressure) TMP at 1.2 bar. The UF was stopped after 13 diafiltration volumes and the permeate flow at the first cycle was 16.0 L/h.m². The dry weight extraction yield was 64%, protein extraction yield was 62% and the volume yield was 78%. The concentrate obtained comprised SDW: 22.4 mg/mL; Prot: 8.7 mg/mL; .A.A.: 1.8 mg/mL; Sugar: 0.54 mg/mL; DNA: 39.1 µg/mL. D-amino acid percentage: 32% D-Ala, 18% D-Thr, PBMC at 1 mg of active dry weight/mL: IL-6: 22303 µg/mL, IL-10: 561 µg/ml, TNF-α: 336 µg/mL. NOx production in mg of active dry weight/mL: 0.02 mg/mL (C1, 0.2 mg/mL (C2), and 2.0 mg/mL (C3): C1: 11.3 µM, C2: 15.3 µM, C3: 13.5 µM. D-amino acid percentage: 32% D-Ala, 18% D-Thr, 10% D-Leu, 44% D-Ser, 26% D-Asx, 23% D-Met, 17% D-Phe, 15% D-Glx, 14% D-Tyr, 9% D-Lys.

Example 4.21

The lysate of example 3.15 was transferred to an MF tank. The TFF installation was similar to example 4.1. The cross flow, for the serpentine mode, was adjusted at 2500 (L/h m2) LHM and the (Trans Membrane Pressure) TMP at 1.0 bar. The UF was stopped after 13 diafiltration volumes and the permeate flow at the first cycle was 15.0 L/h.m2. The dry weight extraction yield was 69%, protein extraction yield was 66% and the volume yield was 77%. The concentrate obtained comprised SDW: 21.4 mg/mL; Prot: 7.6 mg/mL; .A.A.: 1.6 mg/mL; Sugar: 0.5 mg/mL; DNA: 25.9 µg/mL. D-amino acid percentage: D-amino acid percentage: 12.5% D-Ala, 3.4% Val, 16.6%, 65% D-Ser, 26.1% D-Asx, 18.8% D-Met, 15.6% D-Glx, 9.1% D-Lys. NOx production in mg of active dry weight/mL: 0.02 mg/mL (C1), 0.2 mg/mL (C2), and 2.0 mg/mL (C3): C1: 10.3 µM, C2: 15.2 µM, C3:12.3 µM.

The liquid form was lyophilized as described in example 4.17. The protein content (Lowry) was: 44 mg protein per gram of lyophilizate. NOx production in mg of active dry weight/mL of lyophilizate: 0.01 mg/mL (C1), 0.1 mg/mL (C2), and 1.0 mg/mL (C3): C1: 6.4 µM, C2: 12.9 µM, C3: 19.4 µM.

Capsules were produced by mixing 50.4 kg of lyophilizate with 64.68 kg of starch 1500 PT, 2.52 kg of magnesium stearate and 50.4 kg of mannitol. NOx production in mg of active dry weight/mL of capsules: 0.01 mg/mL (C1), 0.1 mg/mL (C2), and 1.0 mg/mL (C3): C1: 6.8 µM, C2: 12.1 µM, C3: 19.1 µM.

Example 5

Example 5A

Effect of the Amount of the "Starting Material" on the Activity of the Bacterial Lysates Measured the Secretion of IL-6 by Human PBMC Preparation of Human PBMC and Cell Culture:

Peripheral blood from healthy donors (Centre de transfusion, Hôpital Universitaire, Geneva) was centrifuged to obtain a buffy coat. The buffy coat was mixed with Hanks' balanced saline solution (HBSS, Sigma, Buchs, Switzerland), layered over Ficoll Paque Plus (Amersham Pharmacia) to 1.077 g/mL and centrifuged (2800 rpm, 20° C., 25 min). Cells harvested from the interphase were washed twice in HBSS at 800 rpm for 15 min at room temperature and the pelleted cells were resuspended in HBSS. The cell counts were performed using a Neubauer cell. All cell cultures were performed in RPMI-1640 medium supplemented with penicillin (100 U/mL), streptomycin (100 µg/mL), L-glutamine (2 mmol/L) and 10% fetal calf serum (FCS), all obtained from Sigma. For in vitro stimulation, the cells were cultured at a concentration of $1 \times 10^6$ viable cells/well.

Stimulation and Measurement of IL-6 in Culture Supernatants:

Peripheral blood mononuclear cells (PBMC) were incubated at 37° C. and under 5% $CO_2$ atmosphere with the products of the invention were tested at 0.25, 0.5, 1, and 2 mg/ml "soluble dry weight, SDW" in RPMI-1640 culture medium.

Figure 2A:
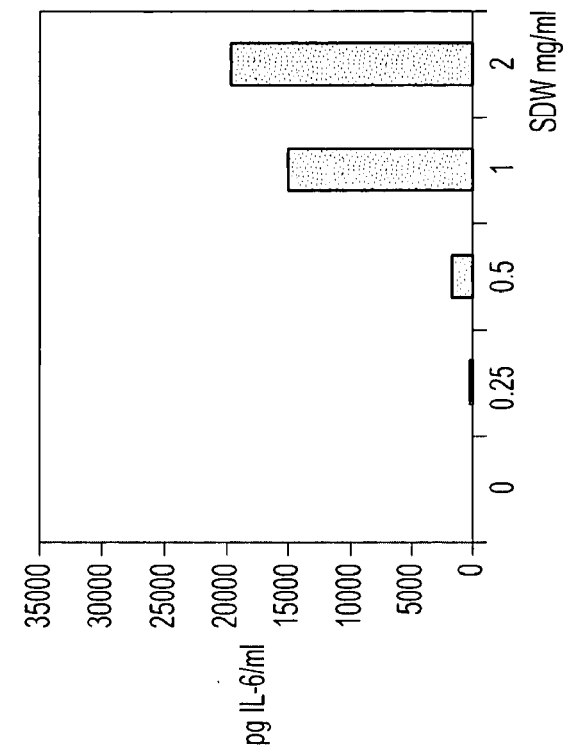
FIGS. 2A and 2B: Activity of extracts in a peripheral blood mononuclear cell (PBMC) test at a starting biomass concentration for lysis of 12.5 g/l (2A) and 25 g/l (2B). (See Example 5A for more details.)
Figure 2B:
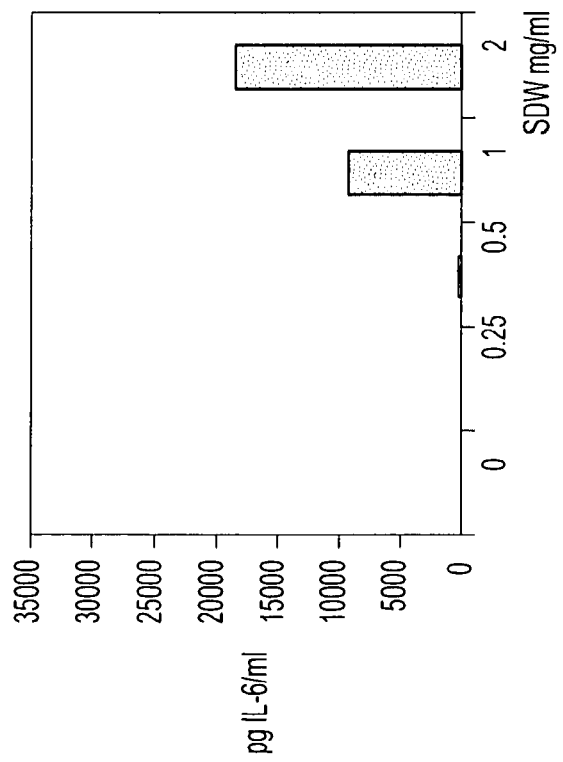
Figure 3A:
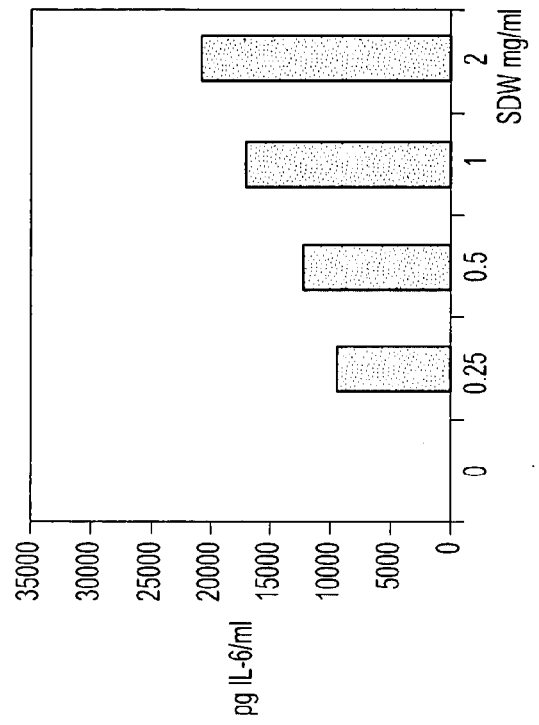
FIGS. 3A and 3B: Activity of extracts in a PBMC test at a starting biomass concentration for lysis of 25 g/l (3A) and 100 g/l (3B).
Figure 3B:
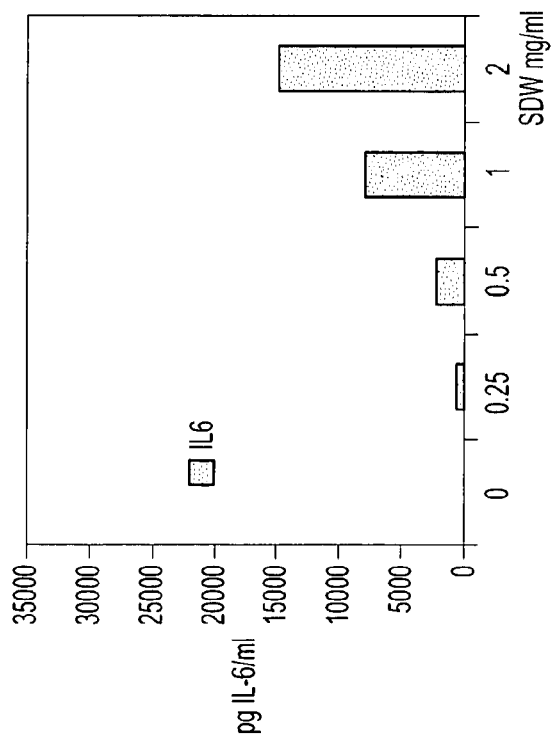

The supernatants of the cultures were harvested after 24 h and the concentration of IL-6 was measured by an enzyme-linked immunosorbent assay (ELISA) (Human IL-6 ELISA Set, BD OptEIA, San Diego, U.S.A.), according to the manufacturer's instructions. The detection limit was 10 µg IL-6/mL. The activity was first tested in the PBMC test. (See FIGS. 2A and 2B, showing the effect of increasing the amount of "starting material" (concentration of bacterial biomass expressed in gram dry weight per liter of lysate) from 12.5 g/l (FIG. 2a) to 25 g/l (FIG. 2B). The activity of the extracts was dependent of the amount of the "starting material" which undergoes the alkaline lysis (12.5 g/l vs 25 g/l). The percentage of NaOH (2% v/v) and the time of the alkaline lysis (72 h) were constant. FIGS. 3A and 3B show the effect of increasing the starting material from 25 g/l to 100 g/l. The time of alkaline lysis was fixed at 168 h and the percentage of NaOH was fixed at 1%.

According to FIGS. 2A, 2B, 3A and 3B, the higher the level of "Starting Material," the higher the resulting activity.

Example 5B

Figure 4B:
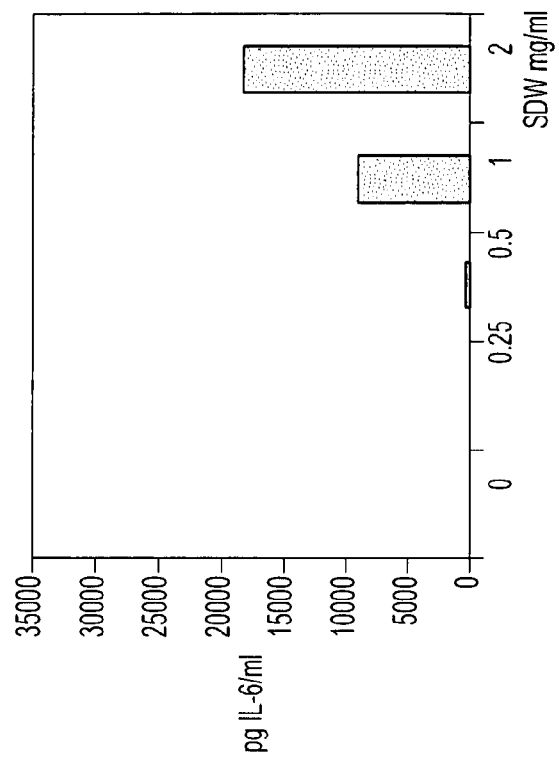
FIGS. 4A and 4B: Activity of extracts in a peripheral blood mononuclear cell (PBMC) test at a lysis time of 24 hours (4A) and 72 hours (4B).
Figure 4A:
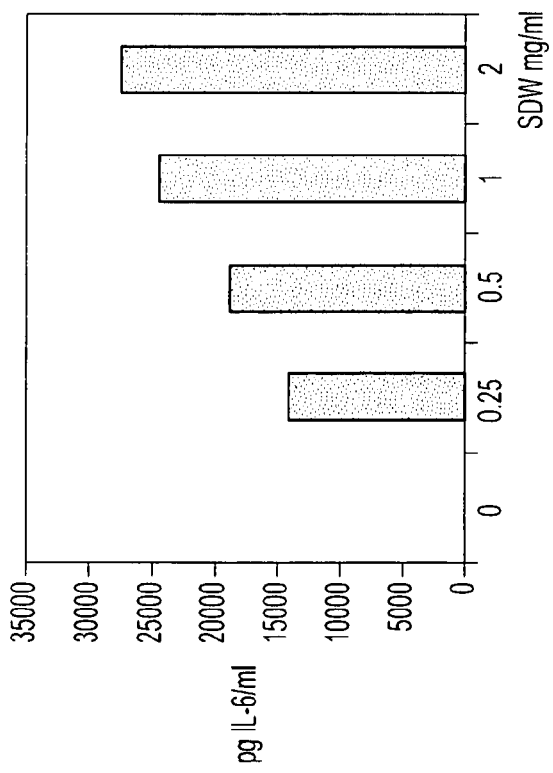

Effect of the Duration of the Lysis on the Activity of the Products of the Invention on the Human PBMC Test The "Starting Material" was 12.5 g/l, and was treated with 2% NaOH during either 24 h (FIG. 4A) or 72 h (FIG. 4B). According to those figures, the longer lysis time resulted in lower activity.

Example 6

Effect of the Initial Percentage of NaOH (v/v) on the Activity of the Bacterial Lysates of the Invention on the Murine Nitric Oxide Test Six-week old male C57/BL6 mice (six weeks old male, SPF quality, Charles Rivier, FR) were killed by $CO_2$ inhalation. The hip, femur, and tibia from the posterior appendage were removed. The bone marrow was extracted from the lumen by injecting Dulbecco's Modified Eagle Medium (DH) through the bone after cutting both end portions. After washing, the stem cells were resuspended (40,000 cells/mL) in DH medium supplemented with 20% horse serum and 30% L929 cell supernatant. The cell suspension was incubated for 8 days in an incubator at 37° C. under 8% $CO_2$ and moisture-saturated atmosphere. Macrophages were then detached with ice-cold PBS, washed and resuspended in DH medium supplemented with 5% fetal calf serum (FCS), amino acids and antibiotics (DHE medium). The cell density was adjusted to 700,000 cells/mL. Aqueous solutions of the products were serially diluted in DHE medium directly in microtiter plates. The products were tested in triplicates and each microtiter plate comprised a negative control composed of medium. The final volume in each well was 100 µL. 100 µL of the cell suspension was added to the diluted products and the cells were incubated for 22 h in an incubator at 37° C., under 8% CO2 and a moisture-saturated atmosphere. At the end of the incubation period, 100 µL of supernatant was transferred to another microtiter plate and the nitrite concentration produced in each supernatant was determined by running a Griess reaction. 100 µL of Griess reagent (5 mg/mL of sulfanilamide+0.5 mg/mL of N-(1-naphtyl)ethylene-diamine hydrochloride) in 2.5% aqueous phosphoric acid, was added to each well. The microtiter plates were read with a spectrophotometer (SpectraMax Plus, Molecular Devices) at 562 nm against a reference at 690 nm. The nitrite concentration was proportional to nitric oxide content being formed. The nitrite content was determined based on a standard curve. The results were given in µM nitric oxide (NO) as mean value±standard deviation and plotted as a dose response curve.

Figure 5:
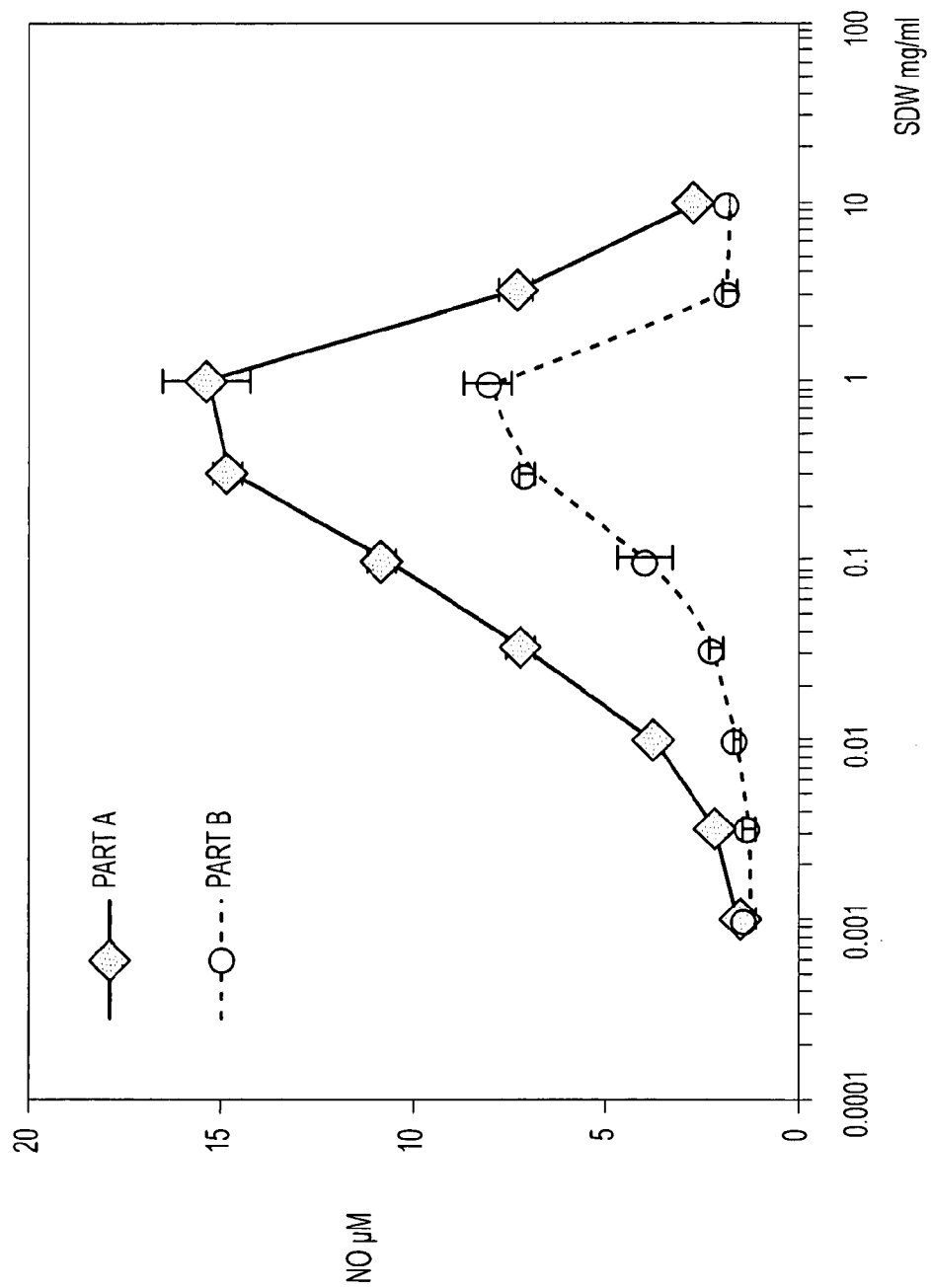
FIG. 5: Effect of concentration of NaOH during lysis on nitrous oxide (NO) activity of macrophages.

In the tests shown in FIG. 5, the amount of starting material (25g/l) and the time of lysis (168 h) were similar, the variable tested was the concentration of NaOH (1% in Part A vs 4% Part B) used to obtain both lysates. Lower activity was observed when 4% NaOH (B in FIG. 5) was used vs 1% NaOH (A in FIG. 5), suggesting a probable alkaline dose-dependant degradation of endotoxin-like molecules.

Depending upon the starting material, concentration of NaOH, and time of lysis, different immunological activities in the NO macrophage test may be generated.

Example 7

Limulus Amoebocyte Lysate Chromogenic (LAL) Test

To determine the presence of endotoxin-like molecules, an LAL test was performed with the Chromogenic-LAL Kit of Bio-Whittaker.

This test is based on activation by lipopolysaccharide (LPS) or products of comparable structure, by an enzymatic cascade present in the LAL. This enzymatic activation is demonstrated by the splitting of a chromogen linked to a peptide by a protease. The enzymatic reaction is carried out at 37° C. and the formation of the chromogen over time is measured at 405 nm. The time necessary to reach 0.2 units of D.O. is recorded and the endotoxic activity calculated in relation to a LPS standard (standard curve).

The results of such an example experiment on extracts according to the invention are expressed in the table below in EU (Endotoxin Unit) in relation to a standardized preparation of $E.\ coli$ LPS (1 EU corresponds to 0.09 ng equivalent LPS).

| Conditions of lysis (Time of lysis, amount of Starting Material, initial percentage of NaOH) | EU/ml | ng equivalent LPS/ml |
|---|---|---|
| T = 24 h-12.5 g/l-2% NaOH | 343 ± 6 | 22 ± 0.4 |
| T = 24 h-12.5 g/l-1% NaOH | 33530 ± 176 | 2163 ± 11 |
| T = 24 h-25 g/l-2% NaOH | 908 ± 5.1 | 58 ± 0.3 |
| T = 24 h-50 g/l-4% NaOH | 48 ± 0.4 | 3 ± 0.1 |
| T = 24 h-50 g/l-3% NaOH | 355 ± 11 | 23 ± 0.7 |
| T = 72 h-12.5 g/l-2% NaOH | <50 | <3 |
| T = 72 h-25 g/l-3% NaOH | 65 ± 0.9 | 4. ± 0.1 |
| T = 72 h-50 g/l-2% NaOH | 196 ± 6 | 13 ± 0.4 |
| T = 72 h-50 g/l-3% NaOH | 45 ± 3 | 3 ± 0.2 |
| T = 72 h-50 g/l-4% NaOH | 162 ± 3 | 11 ± 0.2 |
| T = 168 h-12.5 g/l-2% NaOH | 26 ± 0.7 | 2 ± 0.1 |
| T = 168 h-12.5 g/l-3% NaOH | 45 ± 3 | 3 ± 0.2 |
| T = 168 h-25 g/l-3% NaOH | 25 ± 1 | 2 ± 0.04 |
| T = 168 h-50 g/l-2% NaOH | 55 ± 1 | 4 ± 0.04 |
| T = 168 h-50 g/l-3% NaOH | 1035 ± 42 | 67 ± 2.7 |
| T = 168 h-50 g/l-4% NaOH | 46 ± 2 | 3 ± 0.1 |
| Water | <0.005 | <0.0003 |

Example 8

Effect of the Embodiments of the Invention in a Urinary Tract $Escherichia\ coli$ Infection Model in an LPS Insensitive Strain of Mice Embodiments according to the invention were tested in an $E.\ coli$ urinary tract infection model in LPS-insensitive mice. (See Hopkins et al., Inheritance of susceptibility to induced $Escherichia\ coli$ bladder and kidney infections in female C3H/HeJ mice, $J\ Infect\ Dis.$ 2003 February 1;187(3):418-23). Three groups of 10-12 week old female C3H/HeJ mice (8 mice in each group) were treated orally with one of three different extracts (see below) for 10 days prior to $E.\ coli$ infection. The C3H/HeJ mice contain a mutation in the toll-like receptor gene TLR4, and are insensitive to TLR4 agonists such as lipopolysaccharides (LPS). Therefore this model is suitable to detect the effects of drugs acting via other routes than TLR4.

The mice were maintained during the treatment period under normal conditions at ambient temperature of 18-26° C. and a relative humidity of 30 to 70%. The light program was set on a light-dark cycle of 12:12 hours. Animals were fed with a standard diet provided by Harlan Sprague Dawley (Indianapolis, Ind.) laboratories. Tap water will be provided ad libitum, unless when indicated herein.

The three extracts tested were:
a) An extract obtained by a strong lysis of 18 $E.\ coli$ strains
b) An extract obtained by a moderate lysis of 18 $E.\ coli$ strains
c) An extract obtained by a mixture of a) and b) (¼ and ¾ respectively)

Twenty-five mg of bacterial extract was given to each mouse orally once a day for 10 consequent days. Mice were inoculated intravesically with phosphate-buffered saline (PBS) or with uropathogenic $E.\ coli$ strain 1677 according to a minimal inoculum protocol that reduces the likelihood of reflux-associated inoculation of the kidneys and induces infections in all animals inoculated. The $E.\ coli$ strain 1677, isolated from the urine of a woman with a febrile UTI, was used in these experiments This strain is O6 and contains genes for, for instance, hemolysin, aerobactin, P fimbriae, and type 1 fimbriae, but not for, for instance, afimbrial adhesin I, cytotoxic necrotizing factor 1, and S fimbriae. To prepare the inoculum, bacteria were grown from frozen stock by 2 passages in tryptose broth (Difco Laboratories), washed with PBS, and resuspended to a concentration of $2 \times 10^{10}$ bacteria/mL. Mice were deprived of water for 1 hour and urine was removed from their bladders immediately before inoculation. Ten microliters of bacterial inoculum were instilled into the bladder by urethral catheterization under isoflurane anesthesia, resulting in a dose of $2 \times 10^8$ $E.\ coli$ per mouse. The animals were allowed to recover from anesthesia and water was given back 1 h later.

Mice were killed 10 days after inoculation to assess the intensities of bladder and kidney infections. The bladder and both kidneys of each animal were removed, weighed, and homogenized in sterile PBS, after which the homogenates were serially plated onto Levine's eosin-methylene blue agar (Difco Laboratories). The number of $E.\ coli$ colonies on each plate was counted after overnight incubation at 37° C. and was used to calculate the total number of bacteria in each bladder or pair of kidneys.

Fisher's protected least significant difference test was used to determine the statistically significant differences between the mean total colony-forming unit (CFU) values for different groups of mice (PBS, untreated infected group, and treated and infected group). The bladder and kidney infection data was transformed using total CFU=log 10 [(CFU+100)/mg tissue], where CFU is the total number of colony-forming units calculated per tissue sample.

Figure 6A:
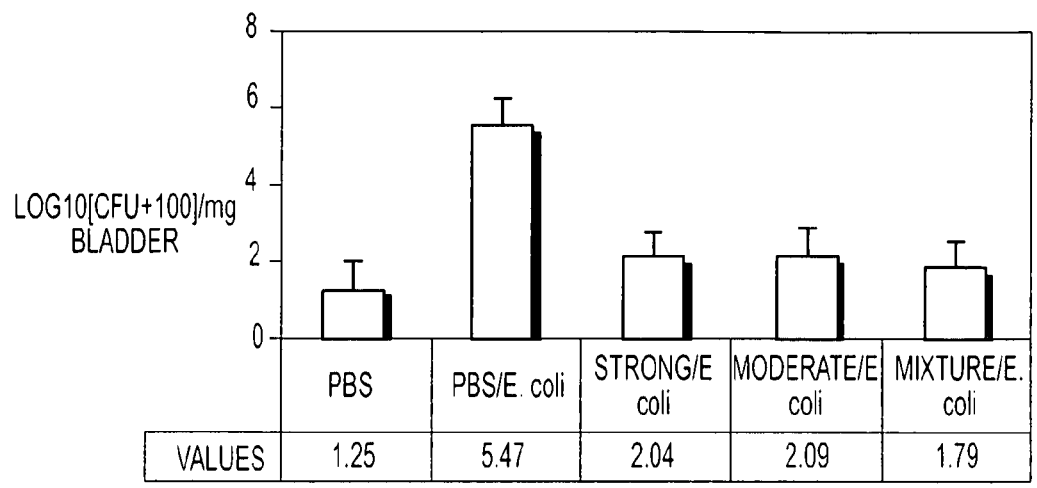
FIGS. 6A and 6B: Mean total colony-forming unit (CFU) values in bladder (6A) and kidney (6B) tissues for different experimental groups.
Figure 6B:
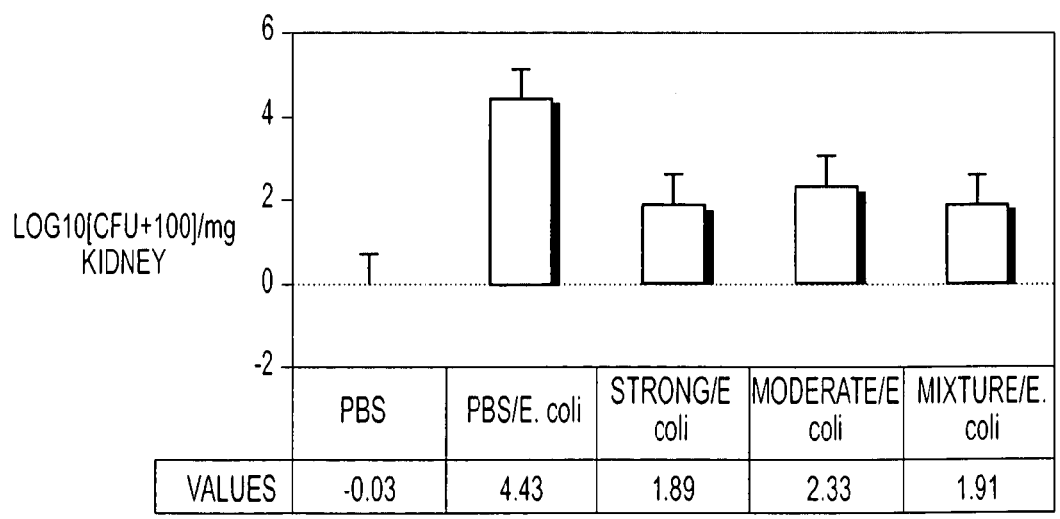

The results obtained are illustrated in FIGS. 6A and 6B, for bladder and kidneys respectively. In summary, the 3 bacterial lysates tested decreased by a factor >3 (bladder) and >2 (kidneys) the logarithmic values obtained, suggesting that the number of colonies cultured from the bladder and the kidneys was decreased by at least a factor of 1000 and 100 respectively. As the results were generated in C3H/HeJ mice, the effects observed are TLR4 independent.

Example 9

Effect of Embodiments of the Invention in a Murine Model of Intraperitoneal $Salmonella\ typhimurium$ Infection in an LPS Sensitive Strain of Mice Three extracts of the invention described in Example 8 were also tested in C57/bl mice, which have a normal LPS-sensitivity. The three extracts tested were:

a) An extract obtained by a strong lysis of 18 *E. coli* strains
b) An extract obtained by a moderate lysis of 18 *E. coli* strains
c) An extract obtained by a mixture of a) and b) (¼ and ¾ respectively).

C57BL/6 mice were kept for 7 days before oral treatment with the substances mentioned above. The experiment consisted of 4 experimental groups—3 groups treated with the compounds of the invention, and a control group. Each experimental group involved 20 mice. Mice in the control group received a sham treatment using oral administration of 0.5 ml water daily for 10 days. For the other groups, the extracts were dissolved daily in distilled water in order to have a single dose in a final volume of 0.5 ml. This 0.5 ml volume was given to each mouse orally once a day for 10 consequent days before all mice were challenged with *Salmonella*. 10 mg of bacterial extract was given to each animal in each administration.

For the challenge, a suspension of *Salmonella typhimurium* strain 415 (I. Mechnokov Institute for Vaccines and Sera, Russian Academy of Medical Sciences) was intraperitoneally injected into each mouse.

A preliminary dose-finding challenge (not shown) ranged from $10^2$ to $10^5$ CFU of Salmonellae per mouse. A dose of $10^4$ CFU was selected for the main experiment, because this dose provided approximately 50% of survivors in untreated animals. After the challenge, mice were kept under the standard conditions for laboratory animals. Daily observation and records of death were performed during a period of 21 days post-infection.

The anti-infective efficacy of compounds (see the tables below) was estimated according to the post-infection survival rate (SR), the post-infection average duration of life (ADL), the defense factor (DF), and the preparation efficacy index (EI), which were calculated for each experimental group. The SR was taken as a percent of alive animals in the experimental group on day 21 post-infection. The ADL, DF and EI were calculated using the following formulas:

$$ADL = (X1 + X2 + \ldots + Xn) : N,$$

where ADL is an average duration of life, X1 to Xn are durations of life post-infection for experimental mice #1 to #n, and N is a total number of animals in the experimental group.

$$DF = CD : ED,$$

where DF is the defense factor, CD is a percent of death in the control group, and ED is a percent of death in the experimental group.

$$EI = [(DF - 1) : DF] \times 100\%,$$

where EI is the preparation efficacy index and DF is the defense factor.

Figure 7:
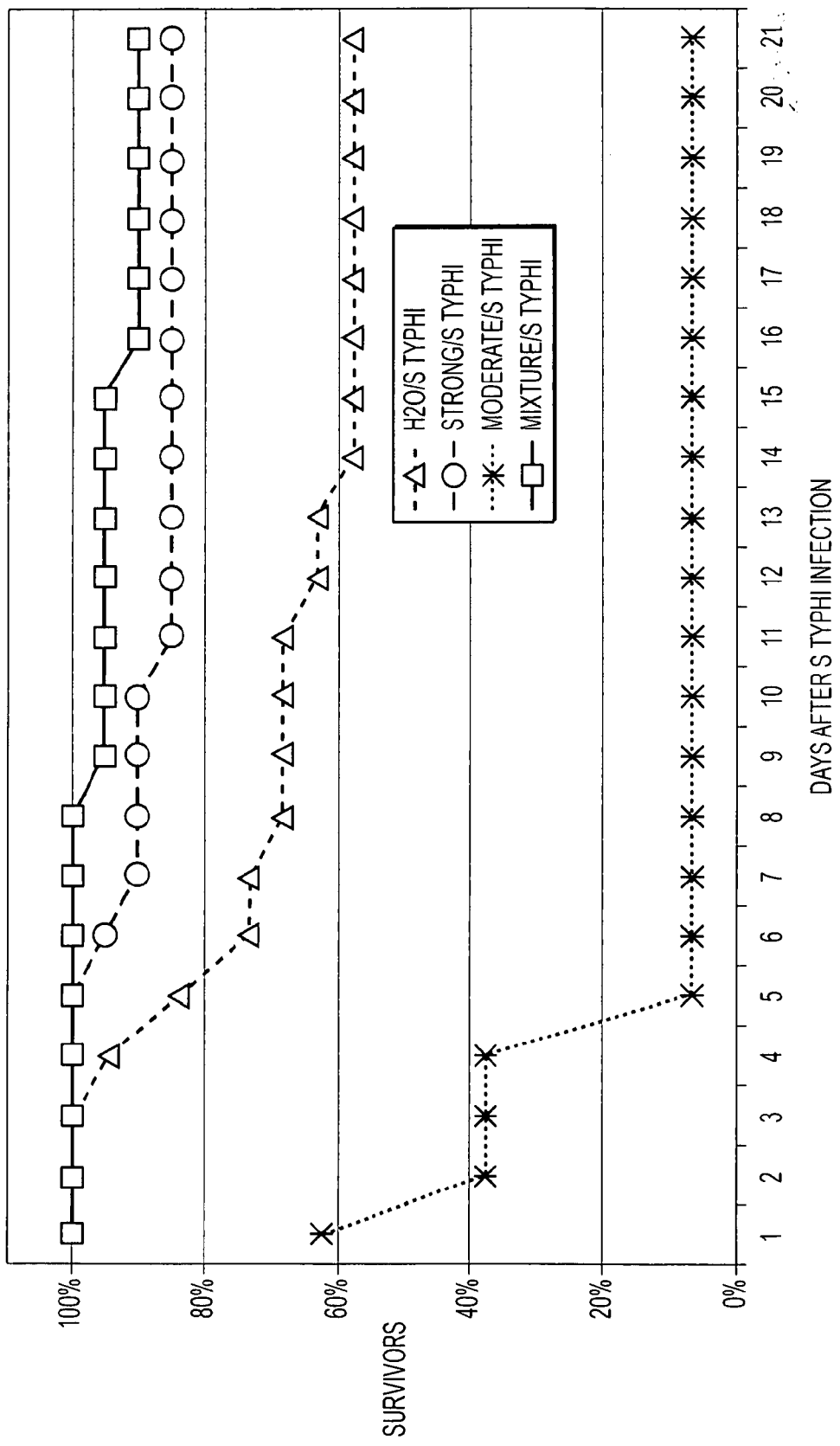
FIG. 7: Death records in experimental groups during the period of 21 days post-infection with $10^4$ CFU of *Salmonella typhimurium*.

Death records in experimental groups during the period of 21 days post-infection with $10^4$ CFU of *Salmonella typhimurium*. The same results are also represented in FIG. 7.

Defense efficacy of extracts in the model of *Salmonella thyphimurium* lethal infection in C57BL/6 mice.

| Pre-Treatment With Substances | Death Rate (%) | Survival Rate (%) | ADL (days) | DF | EI (%) |
|---|---|---|---|---|---|
| H₂O | 42 | 58 | 15.3 | 1 | 0 |
| Strong | 15 | 85 | 19.1 | 2.8 | 64 |
| Moderate | 94 | 6 | 3.3 | No defense | No efficacy |
| Mixture | 10 | 90 | 20.2 | 4.2 | 76 |

Extracts (a) and (c) made from a strong alkaline lysis (strong) and from a mixture of strong and moderate lyses (mixture) were well tolerated. The extract (b) made from a moderate lysis (moderate) demonstrated a higher toxicity than the others. A decrease in the mouse body size, and delays in the mouse growth were observed, although not measured, in the group treated with extract (b). Four of 20 mice in experimental group (b) or "moderate" died during the course of treatment. Thus, only 16 mice in this group were challenged later with Salmonellae.

In the control group of mice pre-treated with water, a survival rate during the period of observation (21 days) was 58%, and the ADL was 15.3 days. Extract (b) appeared to provide no defense against *Salmonella* infection, and the extract accelerated the death of infected animals. Specifically, 90% of mice died by the day 7 post-infection, and the ADL was 3.3 days. A survival rate in this group by the day 21 post-infection was as low as 6% (see tables above and FIG. 7).

In contrast, extracts (a) and (c), made from a strong lysis (Strong) or from a mixture of strong and moderate lyses (Mixture) increased the resistance of mice to infection with *Salmonella thyphimurium*. Both substances showed good protection efficacy. Specifically, survival rate post-challenge with extract (c), (Mixture), was 90%, while with extract (a), (Strong), it was 85% (tables above and FIG. 7).

Additional Examples

An extract from one or more *Escherichia coli* bacterial strains, wherein, during the preparation of the extract, the one or more bacterial strains are lysed at a pH of greater than 12, and the extract is treated so as to remove nucleic acids; and wherein the extract does not pose a risk of prion diseases upon administration to a patient.

The extract of the preceding paragraph obtained from at least one *E. coli* strain chosen from: NCTC: 8603, 8621, 8622, 8623, 9026, 9111, 9119, 9707, and 9708, and I: 081, 082, 083, 084, 085, 086, 087, 088, and 089.

The extract of the preceding paragraph obtained from each of the following *E. coli* strains: NCTC: 8603, 8621, 8622, 8623, 9026, 9111, 9119, 9707, and 9708 and I: 081, 082, 083, 084, 085, 086, 087, 088, and 089.

| Pre-treatment | Number of mice before challenge | 1 | 2 | 3 | 4 | 5 | 6 | 7 | 8 | 9 | 10 | 11 | 12 | 13 | 14 | 15 | 16 | 17 | 18 | 19 | 20 | 21 | Death (%) | Survival Rate (%) |
|---|---|---|---|---|---|---|---|---|---|---|---|---|---|---|---|---|---|---|---|---|---|---|---|---|
| H₂O | 19 | — | — | — | 1* | 2 | 2 | — | 1 | — | — | — | 1 | — | 1 | — | — | — | — | — | — | — | 42 | 58 |
| Strong | 20 | — | — | — | — | — | — | 1 | 1 | — | — | — | 1 | — | — | — | — | — | — | — | — | — | 15 | 85 |
| Moderate | 16 | 6 | 4 | — | — | 5 | — | — | — | — | — | — | — | — | — | — | — | — | — | — | — | — | 94 | 6 |
| Mixture | 20 | — | — | — | — | — | — | — | — | 1 | — | — | — | — | — | — | 1 | — | — | — | — | — | 10 | 90 |

*The number of mice found dead on the day shown.

The extract of any of the three preceding paragraphs, wherein the extract comprises less than 100 μg/mL nucleic acid.

The extract of any of the preceding paragraphs, wherein the extract comprises at least 0.3 mg/mL of saccharides.

The extract of any of the preceding paragraphs, wherein at least one saccharide is selected from the group consisting of monosaccharides, disaccharides, and polysaccharides.

The extract of the preceding paragraph, wherein at least one polysaccharide is a branched polysaccharide.

The extract of any of the preceding paragraphs, wherein at least one saccharide is chemically modified.

The extract of any of the preceding paragraphs, wherein the extract comprises between 0.3 and 4.5 mg/mL of saccharides.

The extract of any of the paragraphs above, wherein lysis is performed at a pH of 12.6 to 13.4.

The extract of any of the preceding paragraphs, wherein the extract is obtained by lysis for a period of 30 to 120 hours with a biomass of 15 to 80 g/L.

The extract of any of the preceding paragraphs, wherein the extract is treated so as to remove particulate and/or insoluble components.

The extract of any of the preceding paragraphs, wherein the extract comprises between 1.5 to 2.5 mg/mL of free amino acids.

The extract of any of the preceding paragraphs, wherein each bacterial strain is cultured in a medium that does not pose a risk of prion diseases.

The extract of any of the preceding paragraphs, wherein each bacterial strain from which the extract is derived is cultured in a vegetal or synthetic medium.

The extract of any of the preceding paragraphs, wherein at least one amino acid chosen from aspartic acid, glutamic acid, serine, histidine, alanine, arginine, tyrosine, methionine, phenylalanine, and lysine is racemized by at least 10%.

The extract of any of the preceding paragraphs, wherein the free amino acids of the extract comprise between 1 and 80% D-amino acids.

The extract of any of the preceding paragraphs, wherein the free amino acids of the extract comprise between 10 and 45% D-amino acids.

The extract of the the preceding paragraph, wherein the free amino acids of the extract comprise between 25 and 35% D-amino acids.

The extract of any of the preceding paragraphs, wherein the extract comprises at least one D-amino acid chosen from D-aspartic acid and D-asparagine, D-glutamic acid and D-glutamine, D-serine, D-methionine, D-histidine, D-alanine, D-arginine, D-phenylalanine, D-tyrosine, D-leucine, D-lysine, D-valine, and D-threonine.

The extract of the preceding paragraph, wherein the concentration of any one D-amino acid comprises between 1 and 50% of the free amino acid concentration.

The extract of the preceding paragraph, wherein the concentration of any one D-amino acid comprises between 10 and 40% of the free amino acid concentration.

The extract of the preceding paragraph, wherein the concentration of any one D-amino acid comprises between 15 and 35% of the free amino acid concentration.

The extract of any of the preceding paragraphs, wherein the extract comprises less than 5000 ng of LPS equivalents by a limulus amoebocyte lysate (LAL) chromogenic test.

The extract of any of the preceding paragraphs, wherein the extract comprises between 8 and 75 mg/mL of one or more proteins.

The extract of any of the preceding paragraphs, wherein the one or more proteins have molecular weights of less than 30 kDa.

The extract of any of the preceding paragraphs, wherein the one or more proteins have molecular weights of less than 10 kDa.

The extract of any of the preceding paragraphs, wherein the survival rate of at least 8 LPS-insensitive mice 13 days after challenge with uropathogenic *E. coli* strain 1677 is at least 70%, wherein the dose of uropathogenic *E. coli* strain 1677 is chosen such that the survival rate of at least 8 control mice is 60% or lower.

The extract of the preceding paragraph, wherein the survival rate is at least 80%.

The extract of the preceding paragraph, wherein the survival rate is at least 90%.

The extract of any of the preceding paragraphs, wherein the survival rate of at least 8 mice with wild-type LPS sensitivity 13 days after challenge with *Salmonella thyphimurium* is at least 70%, wherein the dose of *Salmonella thyphimurium* is chosen such that the survival rate of at least 8 control mice is 60% or lower.

The extract of the preceding paragraph, wherein the survival rate is at least 80%.

The extract of the preceding paragraph, wherein the survival rate is at least 90%.

A pharmaceutical composition comprising the extract of any of the above paragraphs.

A method of treating a subject suffering from or at risk of developing a digestive or urinary tract disorder, comprising administering an effective amount of any of the extracts of the above paragraphs to said subject.The method of any of the preceding paragraphs, wherein said subject is a human.

The method of any of the preceding paragraphs, wherein the digestive or urinary tract disorder is chosen from urethritis, tubulo-interstitial nephritis, obstructive pyelonephritis, urinary tract infections due to obstructive and reflux uropathy, cystitis including chronic cystitis, prostatitis including chronic prostatitis, prostatocystitis, female pelvic inflammatory diseases, Crohn's disease, and irritable bowel syndrome.

A process for preparing an extract obtained from one or more strains of *E. coli* comprising:
  (a) culturing each strain in a medium that does not pose a risk of prion diseases;
  (b) lysing each strain at a pH greater than 12; and
  (c) passing the product of (b) at least once through a microfilter and at least once through an ultrafilter.

The process of the preceding paragraph, wherein the extract is obtained from at least one *E. coli* strain chosen from: NCTC: 8603, 8621, 8622, 8623, 9026, 9111, 9119, 9707, and 9708 and I: 081, 082, 083, 084, 085, 086, 087, 088, and 089.

The process of the preceding paragraph, wherein the extract is obtained from each of the following *E. coli* strains: NCTC: 8603, 8621, 8622, 8623, 9026, 9111, 9119, 9707, and 9708 and I: 081, 082, 083, 084, 085, 086, 087, 088, and 089.

The process of any of the preceding paragraphs, wherein the lysis is carried out at an initial pH greater than 12.5.

The process of any of the preceding paragraphs, wherein the lysis is carried out at an initial pH of 12.6 to 13.4.

The process of any of the preceding paragraphs, wherein the lysis is carried out at an initial hydroxide ion concentration of 0.1 N to 1.1N.

The process of any of the preceding paragraphs, wherein the lysis is carried out at an initial hydroxide ion concentration of 0.2N to 1 N.

The process of any of the preceding paragraphs, wherein the lysis is carried out for a period of 20 hours to 10 days at 30-60° C.

The process of any of the preceding paragraphs, wherein the lysis is carried out for a period of 40 hours to 72 hours at 35° C. to 40° C.

The process of any of the preceding paragraphs, wherein the microfilter is 0.45 microns and the ultrafilter is 30 KDa.

The process of any of the preceding paragraphs, further comprising passing the product of (c) through a second microfilter at 0.2 microns.

The process of any of the preceding paragraphs, wherein part (c) is performed by tangential flow filtration.

The process of the preceding paragraph, wherein the tangential flow filtration is performed for 5 to 15 cycles.

The process of any of the preceding paragraphs, wherein the tangential flow filtration is performed as set forth in FIG. 1.

The process of any of the preceding paragraphs, wherein the tangential flow filtration is performed as set forth in FIG. 1, in serpentine mode.

The process of any of the preceding paragraphs, wherein part (b) is carried out with 10-120 g/l bacterial dry weight of material.

The process of any of the preceding paragraphs, wherein part (b) is carried out with 15-80 g/l bacterial dry weight of material.

A product obtained by any of the processes of the preceding paragraphs.

A method of treating a subject suffering from or at risk of developing a digestive or urinary tract disorder, comprising administering an effective amount of any of the product of any one of the processes of the above paragraphs to said subject.

The method of the preceding paragraph wherein the subject is a human.

What is claimed is:

1. An isolated extract which preserves and/or retains saccharide components from a mixture of *Escherichia coli* (*E. coli*) bacterial strains, wherein the extract comprises less than 100 pg/ml nucleic acids, at least 0.3 mg/mL of saccharides, one or more amino acids wherein 1-80 % of said one or more amino acids is racemized from L to D, and between 8 and 75 mg/mL of one or more proteins, wherein said one or more proteins has a molecular weight of less than 30 kDa.

2. The extract of claim 1 obtained from *E. coli* strains chosen from: NCTC: 8603, 8621, 8622, 8623, 9026, 9111, 9119, 9707, and 9708, and I: 081, 082, 083, 084, 085, 086, 087, 088, and 089.

3. The extract of claim 1, wherein the extract comprises between 0.3 and 4.5 mg/mL of saccharides.

4. The extract of claim 3, wherein at least one saccharide, is selected from the group consisting of monosaccharides, disaccharides, and polysaccharides, which may be branched polysaccharides.

5. The extract of claim 1, wherein the extract comprises between 1.5 and 2.5 mg/mL of free amino acids chosen from aspartic acid, glutamic acid, serine, histidine, alanine, arginine, tyrosine, methionine, phenylalanine, and lysine; and wherein at least 10 % of one or more of said free amino acids is racemized from L to D.

6. The extract of claim 1, wherein the extract comprises between 10 and 45 % D-amino acids.

7. The extract of claim 1, wherein the extract comprises between 25 and 35 % D-amino acids.

8. The extract of claim 1, wherein the extract comprises at least one D-amino acid chosen from D- aspartic acid and D-asparagine, D-glutamic acid and D-glutamine, D-serine, D-methionine, D-histidine, D-alanine, D-arginine, D-phenylalanine, D-tyrosine, D-leucine, D-lysine, D-valine, and D-threonine.

9. A pharmaceutical composition comprising the extract of claim 1 and a pharmaceutically acceptable vehicle.

10. A method of stimulating an immune response in a subject comprising administering to said subject an effective amount of the extract of claim 1.

11. A method of stimulating an immune response in a subject comprising administering to said subject an effective amount of the pharmaceutical composition of claim 9.

12. The method of claim 11, wherein said subject is human or domestic animal, and wherein said subject is susceptible to a digestive or urinary tract disorder or at risk of developing a digestive or urinary tract disorder.

13. The method of claim 12, wherein said digestive or urinary tract disorder is selected from the group consisting of urethritis, tubule-interstitial nephritis, obstructive pyelonephritis, urinary tract infections due to obstructive and reflux uropathy, cystitis, chronic cystitis, prostatitis, prostatocystitis, female pelvic inflammatory diseases, Crohn's disease, and irritable bowel syndrome.

* * * * *

UNITED STATES PATENT AND TRADEMARK OFFICE
CERTIFICATE OF CORRECTION

| | | |
|---|---|---|
| PATENT NO. | : 9,198,961 B2 | Page 1 of 1 |
| APPLICATION NO. | : 14/597254 | |
| DATED | : December 1, 2015 | |
| INVENTOR(S) | : Jacques Alain Bauer et al. | |

It is certified that error appears in the above-identified patent and that said Letters Patent is hereby corrected as shown below:

In the Specification

Column 8, Line 25, please replace "to 10 mg/mi" with --to 10 mg/ml--
Column 8, Line 26, please replace "responses ranging from 3 µM to 100 µµM" with --responses ranging from 3 µM to 100 µM--
Column 8, Line 63, please replace "model is at least 70%, at least 80%, at least 80%, at least 90%," with --model is at least 70%, at least 80%, at least 85%, at least 90%,--
Column 9, Line 8, please replace "70%, at least 80%, at least 80%, at least 90%, or at least 95%." with --70%, at least 80%, at least 85%, at least 90%, or at least 95%.--
Column 14, Line 41, please replace "performedr" with --performed--
Column 22, Line 6, please replace "mL: IL-6: 9232 µg/ml" with --mL: IL-6: 9232 pg/ml--
Column 22, Line 66, please replace "µg/ml" with --pg/ml--
Column 22, Line 67, please replace "µg/ml" with --pg/ml--
Column 23, Line 16, please replace "µg/ml" with --pg/ml--
Column 23, Line 17, please replace "µg/ml" with --pg/ml--
Column 23, Line 33, please replace "µg/ml" with --pg/ml--
Column 23, Line 34, please replace "µg/ml" with --pg/ml--
Column 23, Line 53, please replace "µg/ml" with --pg/ml--
Column 23, Line 54, please replace "µg/ml" with --pg/ml--
Column 25, Line 58, please replace "10 µg" with --10 pg--

In the claims

Column 33, Claim 1, Line 43, please replace "pg/ml" with --µg/ml--

Signed and Sealed this
Twenty-third Day of February, 2016

Michelle K. Lee
*Director of the United States Patent and Trademark Office*